United States Patent [19]

Reuschling et al.

[11] Patent Number: 5,723,450
[45] Date of Patent: *Mar. 3, 1998

[54] SUBSTITUTED PYRIDINES, THEIR PREPARATION, AND THEIR USE AS PESTICIDES AND FUNGICIDES

[75] Inventors: Dieter Bernd Reuschling, Butzbach; Adolf Heinz Linkies, Frankfurt; Volkmar Wehner, Sandberg; Rainer Preuss, Hofheim; Wolfgang Schaper, Diedorf; Harald Jakobi, Frankfurt; Peter Braun, Nieder-Olm; Werner Knauf, Eppstein; Burkhard Sachse, Kelkheim; Anna Waltersdorfer, Frankfurt; Manfred Kern, Lörzweiler; Peter Lümmen, Niedernhausen; Werner Bonin, Kelkheim, all of Germany

[73] Assignee: Hoechst Schering AgrEvo GmbH, Berlin, Germany

[*] Notice: The term of this patent shall not extend beyond the expiration date of Pat. No. 5,650,417.

[21] Appl. No.: 304,382

[22] Filed: Sep. 12, 1994

[30] Foreign Application Priority Data

Sep. 14, 1993 [DE] Germany ............................ 43 31 179.2

[51] Int. Cl.[6] ..................... C07D 213/30; C07D 213/32; C07D 213/38; A61K 31/44
[52] U.S. Cl. ................. 514/63; 514/352; 514/278; 514/349; 514/318; 514/345; 504/100; 546/304; 546/14; 546/15; 546/297; 546/194; 546/312; 546/296; 546/298; 546/301; 546/303
[58] Field of Search ................... 546/304, 14, 15, 546/297, 194, 312, 296, 301, 303; 514/352, 63, 278, 349, 318, 345; 504/100

[56] References Cited

U.S. PATENT DOCUMENTS

| | | | |
|---|---|---|---|
| 3,639,413 | 2/1972 | Domenico | 260/294.8 |
| 3,682,936 | 8/1972 | Tarba | 260/297 R |
| 4,180,670 | 12/1979 | Edington et al. | 546/284 |
| 4,835,279 | 5/1989 | Lee et al. | 546/315 |

FOREIGN PATENT DOCUMENTS

| | | |
|---|---|---|
| 0182769 | 5/1986 | European Pat. Off. . |
| A-410762 | 1/1991 | European Pat. Off. . |
| 0476607 | 3/1992 | European Pat. Off. . |
| 0480258 | 4/1992 | European Pat. Off. . |
| 3731626 | 3/1989 | Germany . |
| 9305050 | 3/1993 | WIPO . |

OTHER PUBLICATIONS

C.A. 93 [1980]: 239243p, Bailey; and month of publication not provided.
C.A. Registry Handbook, Number Section, Printed Issues +Microfilm 1965–1991; Columbus, US. CAS RN 39077–45–7 to 39077–47–9, 72945–10–9, 76411–59–1, 26885–30–3, 78526–47–3; 135606–38–1, 37023–09–0 (1965–1991) month of publication not provided.
Gogte, V.N. et al. *Indian J. Chem.* 17B, 230–232 (1979).
Kusaba, T. et al. *Chemical Abstract Services*, CA120:99423 (Oct. 12, 1993).
Bernardi, R. et al. *Chemical Abstract Services*, CA113:23630 (1990).

*Primary Examiner*—Mukund J. Shah
*Assistant Examiner*—King Lit Wong
*Attorney, Agent, or Firm*—Curtis, Morris & Safford, P.C.

[57] ABSTRACT

The invention relates to compounds of the formula

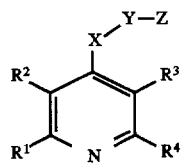

in which $R^1$, $R^2$, $R^3$ and $R^4$ are H, halogen, an aliphatic radical or an aromatic radical, X is O, S or optionally substituted imino, Y is a bond or an optionally substituted bivalent hydrocarbon radical and Z is optionally substituted cycloalkyl or cycloalkenyl. The invention furthermore relates to processes for their preparation and their use as pesticides, in particular as insecticides, acaricides and fungicides.

11 Claims, No Drawings

SUBSTITUTED PYRIDINES, THEIR PREPARATION, AND THEIR USE AS PESTICIDES AND FUNGICIDES

The invention relates to novel substituted 4-amino- and 4-hydroxypyridines, their preparation, and their use as pesticides, in particular as insecticides, acaricides and fungicides.

It has already been disclosed that certain substituted 4-aminopyridines and 4-hydroxypyridines show a fungicidal, acaricidal and insecticidal action (cf. WO 93/05050). However, the biological action of these compounds, in particular at low application rates and concentrations, is not satisfactory in all application ranges.

Novel substituted 4-amino- and 4-hydroxypyridines of the formula 1 have been found, which are biologically active.

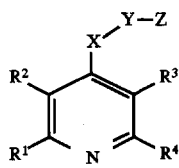

The invention therefore relates to compounds of the formula 1 and their salts, in which (1) $R^1$, $R^2$, $R^3$ and $R^4$ are the same or different radicals from the series
$(C_1-C_4)$-alkyl,
$(C_2-C_4)$-alkenyl,
$(C_1-C_4)$-alkoxy
$(C_2-C_4)$-alkenyloxy,
halo-$(C_1-C_4)$-alkyl,
halo-$(C_2-C_4)$-alkenyl,
halo-$(C_1-C_4)$-alkoxy,
halo-$(C_2-C_4)$-alkenyloxy,
R—O—CH$_2$—,
R—O—CO—,
halo-$(C_1-C_4)$-alkoxymethyl,
halo-$(C_2-C_4)$-alkenyloxymethyl,
halo-$(C_1-C_4)$-alkoxycarbonyl,
halo-$(C_2-C_4)$-alkenyloxycarbonyl,
$(C_1-C_4)$-alkylthio,
$(C_2-C_4)$-alkenylthio,
$(C_1-C_4)$-alkylsulfinyl,
$(C_2-C_4)$-alkenylsulfinyl
$(C_1-C_4)$-alkylsulfonyl,
$(C_2-C_4)$-alkenylsulfonyl,
aryl,
substituted amino,
cyano,
halogen and
hydrogen;
R is
$(C_1-C_{10})$-alkyl,
$(C_2-C_{10})$-alkenyl
$(C_2-C_{10})$-alkynyl,
$(C_3-C_8)$-cycloalkyl or
aralkyl;
aryl is defined as below under (4);
aralkyl is aryl-$(C_1-C_4)$-alkyl;

(2) X is O, S, NH, NR or NOR, R being defined as above under (1);

(3) Y is a bond or a bivalent hydrocarbon radical having 1 to 6 carbon atoms, in which a methylene group can be replaced by an oxygen atom, and which is optionally substituted by one or more, preferably up to three, identical or different radicals from the series
$(C_1-C_7)$-alkyl
preferably straight-chain $(C_1-C_4)$-alkyl or branched $(C_3-C_7)$-alkyl,
$(C_2-C_4)$-alkenyl,
$(C_3-C_4)$-alkynyl,
halogen-$(C_1-C_4)$-alkyl or
halogen;

(4) Z is $(C_3-C_8)$-cycloalkyl or $(C_5-C_8)$-cycloalkenyl, being possible in the carbocycle for CH$_2$ to be replaced by NR$^5$, and R$^5$ is phenyl or substituted phenyl, it being possible for the $(C_3-C_8)$-cycloalkyl or the $(C_5-C_8)$-cycloalkenyl radical to be substituted by one or more, preferably up to three, identical or different radicals from the series
$(C_5-C_{18})$-alkyl
$(C_5-C_{18})$alkenyl,
$(C_5-C_{12})$-alkoxy,
$(C_5-C_{18})$-alkenyloxy,
$(C_5-C_8)$-alkanoyloxy,
$(C_5-Cl_{12})$-acyl,
$(C_5-C_{12})$-alkoxycarbonyl,
$(C_5-C_{12})$-alkenyloxycarbonyl,
SiR$^6$R$^7$R$^8$,
NR$^9$R$^{10}$,
hydroxyl,
oxo,
halogen,
aryl,
$(C_2-C_{18})$-alkanediyl,
$(C_1-C_{18})$-alkanediyldioxy,
$(C_1-C_{13})$-alkyloximino and
$(C_2-C_{18})$-alkylidene, it being possible for alkyl, alkenyl, alkanediyl, alkylidene and radicals derived therefrom, such as alkoxy, to be unbranched or branched and one or more, preferably up to three, methylene groups to be replaced by heteroatoms/ groups, such as O, NR$^{11}$ or SiR$^{12}$R$^{13}$ and moreover for 3 to 6 carbon atoms to form a cycle, and which are optionally substituted by one or more, preferably up to three, in the case of halogen up to the maximum number, of identical or different radicals from the series halogen, halo-$(C_1-C_4)$-alkyl, $(C_3-C_8)$-cycloalkyl, $(C_1-C_8)$-acyl, phenoxy or substituted phenoxy, phenyl or substituted phenyl, phenylthio or substituted phenylthio, R$^{11}$ being hydrogen, $(C_1-C_4)$-alkyl or $(C_1-C_4)$-acyl and R$^{12}$ and R$^{13}$ being identical or different and independently of one another being $(C_1-C_4)$-alkyl, phenyl or substituted phenyl, R$^6$, R$^7$ and R$^8$ are independently of one another $(C_1-C_4)$-alkyl, phenyl and/or substituted phenyl and R$^9$ and R$^{10}$ independently of one another can be $(C_1-C_4$-acyl, $(C_3-C_6)$-cycloalkyl, phenyl and/or substituted phenyl;

aryl is a phenyl group which is optionally substituted by one or more, preferably up to three, identical or different groups from the series
halogen,
$(C_3-C_8)$-cycloalkyl,
$(C_3-C_8)$-cycloalkenyl,
phenoxy,
substituted phenoxy,
phenylthio,
substituted phenylthio,
phenyl,
substituted phenyl,

NO$_2$,

acetoxy,
hydroxyl,
cyano,
SiR$^6$R$^7$R$^8$,
O—SiR$^6$R$^7$R$^8$,
NR$^{15}$R$^{16}$,
S(O)R$^{17}$,
SO$_2$R$^{17}$,
(C$_1$–C$_{12}$)-alkyl,
(C$_1$–C$_{12}$)-alkenyl,
(C$_1$–C$_7$)-alkoxy and
(C$_1$–C$_7$)-alkylthio, R$^{14}$ is (C$_1$–C$_7$)-alkyl, halo-(C$_1$–C$_7$)-alkyl, (C$_3$–C$_7$)-cycloalkyl, halo-(C$_3$–C$_7$)-cycloalkyl, (C$_1$–C$_7$)-alkoxy, phenyl or substituted phenyl;

R$^6$, R$^7$ and R$^8$ have the meaning as above;

R$^{15}$ and R$^{16}$ independently of one another are hydrogen, (C$_1$–C$_4$)-alkyl and/or (C$_1$–C$_4$)-acyl;

R$^{17}$ is (C$_1$–C$_{10}$)-alkyl, phenyl or substituted phenyl, in (C$_1$–C$_{12}$)-alkyl and (C$_2$–C$_{12}$)-alkenyl the hydrocarbon chain can be unbranched or branched and one or more CH$_2$ groups can be replaced by hetero atoms/groups such as O, S, SO, SO$_2$, NR$^{11}$ or SiR$^{12}$R$^{13}$;

R$^{11}$, R$^{12}$ and R$^{13}$ have the meaning as above; the (C$_1$–C$_{12}$)-alkyl or (C$_2$–C$_{12}$)-alkenyl radical with or without the abovementioned variations (replacement of CH$_2$) can additionally be substituted by one or more, preferably up to three, identical or different groups from the series halogen, halo-(C$_1$–C$_4$)-alkoxy, hydroxyl, (C$_3$–C$_8$)-cycloalkyl, (C$_3$–C$_8$)-cycloalkenyl, (C$_1$–C$_4$)-acyl, phenoxy, substituted phenoxy, phenyl, substituted phenyl, phenylthio and substituted phenylthio;

(C$_1$–C$_7$)-alkoxy and (C$_1$–C$_7$)-alkylthio can be unbranched or branched and one or more, preferably up to three, CH$_2$ groups therein can be replaced by O, and moreover can be substituted by one or more, preferably up to three, in the case of halogen up to the maximum, identical or different groups from the series halogen, phenyl, substituted phenyl, (C$_3$–C$_8$)-cycloalkyl, (C$_2$–C$_8$)-cycloalkenyl, phenoxy and substituted phenoxy.

If specifically not defined differently, in the above formula 1 "halogen" is to be understood as meaning a fluorine, chlorine, bromine or iodine atom, preferably a fluorine, chlorine or bromine atom;

the expression "alkyl" is to be understood as meaning an unbranched or branched hydrocarbon radical containing e.g. the methyl, ethyl, propyl, 1-methylethyl, 1-methylpropyl, 2-methylpropyl or 1,1-dimethylethyl radical, the pentyl, 2-methylbutyl or the 1,1-dimethylpropyl radical, or the hexyl, heptyl, octyl, 1,1,3,3-tetramethylbutyl, nonyl or decyl radical;

"alkenyl" and "alkynyl" are understood as meaning monounsaturated radicals derived from these alkyl radicals;

the expression "cycloalkyl" is preferably understood as meaning the cyclopropyl, cyclobutyl, cyclopentyl, cyclohexyl, cycloheptyl or cyclooctyl group;

the expression "cycloalkenyl" is preferably understood as meaning the cyclopentenyl, cyclohexenyl, cycloheptenyl or cyclooctenyl group;

the expression "alkoxy" is understood as meaning an alkoxy group whose hydrocarbon radical has the meaning indicated under the expression "alkyl";

the expression "cycloalkoxy" is understood as meaning a cycloalkoxy group whose hydrocarbon radical has the meaning indicated under "cycloalkyl";

the expression "alkylthio" is understood as meaning an alkylthio group whose hydrocarbon radical has the meaning indicated under the expression "alkyl" (the same applies for "alkylsulfinyl" and "alkylsulfonyl");

the expression "haloalkyl" is understood as meaning an alkyl group mentioned under the expression "alkyl", in which one or more hydrogen atoms are replaced by the abovementioned halogen atoms, preferably chlorine or fluorine, such as, for example, the trifluoromethyl group, the 2,2,2-trifluoroethyl group, the chloromethyl or fluoromethyl group, the difluoromethyl group or the 1,1,2,2-tetrafluoroethyl group (the same applies for "haloalkenyl");

the expression "haloalkoxy" is understood as meaning a haloalkoxy group whose halohydrocarbon radical has the meaning indicated under the expression "haloalkyl";

"substituted phenyl" is understood as meaning a phenyl radical which carries one or more, preferably up to three, identical or different substituents from the series halogen, (C$_1$–C$_4$)-alkyl, halo-(C$_1$–C$_4$)-alkyl, hydroxy-(C$_1$–C$_4$)-alkyl, (C$_1$–C$_4$)-alkoxy, halo-(C$_1$–C$_4$)-alkoxy, phenoxy, phenyl, nitro, hydroxyl, cyano, (C$_1$–C$_4$)-alkanoyl, benzoyl, (C$_1$–C$_4$)-alkanoyloxy, (C$_1$–C$_4$)-alkoxycarbonyl;

"substituted amino" is understood as meaning an amino group which is substituted by one or two (C$_1$–C$_4$)-alkyl groups or a (C$_1$–C$_4$)-alkanoyl group;

a "bivalent hydrocarbon radical having 1 to 6 carbon atoms" is understood as meaning a radical derived from n-alkanes or n-alkenes by removing one hydrogen atom from each of the two terminal carbon atoms of the chain, such as methylene, ethanediyl, trimethylene or tetramethylene, "acyl" is in particular understood as meaning an alkanoyl radical, such as acetyl, propionyl, butyryl, valeryl, or lauroyl, or an alkoxycarbonyl radical.

The explanation given above applies correspondingly for homologs or radicals derived therefrom.

The substituents of (C$_3$–C$_8$)-cycloalkyl and (C$_5$–C$_8$)-cycloalkenyl defined above under (4) can be cis or trans to Y. The cis-position is preferred and if only one substituent is present it should be in the 4-position in the case of cyclohexyl.

Preferred compounds of the formula I and their salts are those in which (1) R$^1$, R$^2$, R$^3$ and R$^4$ are the same or different radicals from the series
(C$_1$–C$_4$)-alkyl,
(C$_2$–C$_4$)-alkenyl,
(C$_1$–C$_4$)-alkoxy
(C$_2$–C$_4$)-alkenyloxy,
halo-(C$_1$–C$_4$)-alkyl,
halo-(C$_2$–C$_4$)-alkenyl,
halo-(C$_1$–C$_4$)-alkoxy,
halo-(C$_2$–C$_4$)-alkenyloxy,
R—O—CH$_2$—,
R—O—CO—,
halo-(C$_1$–C$_4$)-alkoxymethyl,
halo-(C$_2$–C$_4$)-alkenyloxymethyl, halo-$(C_1-C_4)$-alkoxycarbonyl,
halo-$(C_2-C_4)$-alkenyloxycarbonyl,
cyano,
halogen and
hydrogen;

R is as defined above, but only has a maximum of 7 carbon atoms and is not cycloalkyl or aralkyl;

(2) X is O, S or NH;

(3) Y is as defined above;

(4) Z is preferably $(C_3-C_8)$-cycloalkyl or alternatively $(C_5-C_8)$-cycloalkenyl, it being possible for $CH_2$ in the carbocycle to be replaced by $NR^5$, and $R^5$ is phenyl or substituted phenyl, it being possible for the $(C_3-C_6)$-cycloalkyl or the $(C_5-C_8)$-cycloalkenyl radical to be substituted by one or more, preferably up to three, identical or different radicals from the series
$(C_5-C_{18})$-alkyl
$(C_5-C_{18})$alkenyl,
$(C_5-C_{12})$-alkoxy,
$(C_5-C_{18})$-alkenyloxy,
$(C_5-C_{12})$-acyl,
$(C_5-C_{12})$-alkoxycarbonyl,
$(C_5-C_{12})$-alkenyloxycarbonyl,
$SiR^6R^7R^8$,
hydroxy,
oxo,
halogen,
aryl,
$(C_2-C_{18})$-alkanediyl,
$(C_1-C_{18})$-alkanediyldioxy,
$(C_1-C_{13})$-alkyloximino and
$(C_2-C_{18})$-alkylidene it being possible for alkyl, alkenyl, alkanediyl, alkylidene and radicals derived therefrom, such as alkoxy, to be unbranched or branched and one or more, preferably up to three, methylene groups to be replaced by heteroatoms/ groups, such as O, $NR^{11}$ or $SiR^{12}R^{13}$, and moreover for 3 to 6 carbon atoms to form a cycle, and being optionally substituted by one or more, preferably up to three, in the case of halogen up to the maximum number of identical or different radicals from the series halogen, halo-$(C_1-C_4)$-alkyl, $(C_3-C_8)$-cycloalkyl, $(C_1-C_8)$-acyl, phenoxy or substituted phenoxy, phenyl or substituted phenyl, $R^{11}$ being $(C_1-C_4)$-acyl and $R^{12}$ and $R^{13}$ being identical or different and independently of one another being $(C_1-C_4)$-alkyl, phenyl or substituted phenyl, $R^6$, $R^7$ and $R^8$ are independently of one another $(C_1-C_4)$-alkyl, phenyl and/or substituted phenyl, and aryl is a phenyl group which is optionally substituted by one or more, preferably up to three, identical or different groups from the series
halogen,
$(C_3-C_8)$-cycloalkyl,
$(C_3-C_8)$-cycloalkenyl,
phenoxy,
substituted phenoxy,
phenyl,
substituted phenyl, $$\overset{O}{\underset{\|}{-C}}-R^{14},$$

$SiR^6R^7R^8$,
$O-SiR^6R^7R^8$,
$NR^{15}R^{16}$,
$(C_1-C_{12})$-alkyl,
$(C_1-C_{12})$-alkenyl and
$(C_1-C_7)$-alkoxy, $R^{14}$ is $(C_1-C_7)$-alkyl, halo-$(C_1-C_7)$-alkyl, $(C_5-C_6)$-cycloalkyl, $(C_1-C_7)$-alkoxy, phenyl or substituted phenyl;

$R^6$, $R^7$ and $R^8$ have the meaning as above;

$R^{15}$ and $R^{16}$ independently of one another are hydrogen, $(C_1-C_4)$-alkyl and/or $(C_1-C_4)$-acyl;

in $(C_1-C_{12})$-alkyl and $(C_2-C_{12})$-alkenyl the hydrocarbon chain can be unbranched or branched and one or more $CH_2$ groups can be replaced by heteroatoms/ groups such as O, $R^{11}$ or $SiR^{12}R^{13}$;

$R^{11}$, $R^{12}$ and $R^{13}$ have the meaning as above; the $(C_1-C_{12})$-alkyl or $(C_2-C_{12})$-alkenyl radical with or without the abovementioned variations (replacement of $CH_2$) can additionally be substituted by one or more, preferably up to 3, identical or different groups from the series halogen, halo-$(C_1-C_4)$-alkoxy, hydroxyl, $(C_3-C_6)$-cycloalkyl, $(C_1-C_4)$-acyl, phenoxy, substituted phenoxy, phenyl and substituted phenyl; $(C_1-C_7)$-alkoxy can be unbranched or branched and one or more, preferably up to three $CH_2$ groups therein can be replaced by O and moreover can be substituted by one or more, preferably up to three, in the case of halogen up to the maximum, identical or different groups from the series halogen, phenyl, substituted phenyl, $(C_3-C_6)$-cycloalkyl, $(C_3-C_8)$-cycloalkenyl, phenoxy and substituted phenoxy.

Particularly preferred compounds of the formula I and their salts are those in which (1) $R^1$, $R^2$, $R^3$ and $R^4$ are the same or different radicals from the series
$(C_1-C_3)$-alkyl,
$(C_2-C_3)$-alkenyl,
$(C_1-C_3)$-alkoxy
$(C_2-C_3)$-alkenyloxy,
halo-$(C_1-C_4)$-alkyl,
halo-$(C_2-C_4)$-alkenyl,
halo-$(C_1-C_4)$-alkoxy,
halo-$(C_2-C_4)$-alkenyloxy,
R—O—$CH_2$—,
R—O—CO—,
halo-$(C_1-C_3)$-alkoxymethyl,
halo-$(C_2-C_3)$-alkenyloxymethyl,
halo-$(C_1-C_3)$-alkoxycarbonyl,
halo-$(C_2-C_3)$-alkenyloxycarbonyl,
cyano,
halogen and
hydrogen;

R is defined as at the beginning, but only has a maximum of 5 carbon atoms and is not alkynyl, cycloalkyl or aralkyl;

(2) X is O, S, NH or NR;

(3) Y is a bond or a bivalent hydrocarbon radical having 1 to 6 carbon atoms, in which a methylene group can be replaced by an oxygen atom, and which is optionally substituted by one or more, preferably up to three, identical or different radicals from the series
$(C_1-C_3)$-alkyl,
branched $(C_3-C_5)$-alkyl,
halo-$(C_1-C_3)$-alkyl or
halogen;

(4) Z is $(C_3-C_6)$-cycloalkyl, it being possible for $CH_2$ in the carbocycle to be replaced by $NR^5$ and $R^5$ being phenyl or substituted phenyl, it being possible for the $(C_3-C_8)$-cycloalkyl or the $(C_5-C_8)$-cycloalkenyl radical to be substituted by one or more, preferably up to three, identical or different radicals from the series
$(C_5-C_{12})$-alkyl,
$(C_5-C_{12})$-alkenyl,
$(C_5-C_{12})$-alkoxy,
$(C_5-C_{12})$-alkenyloxy,
$(C_5-C_{12})$-acyl,
$(C_5-C_{12})$-alkoxycarbonyl,
$(C_5-C_{12})$-alkenyloxycarbonyl,
$SiR^6R^7R^8$,
hydroxyl,
oxo,
halogen,
aryl,
$(C_2-C_{18})$-alkanediyl,
$(C_1-C_{18})$-alkanediyldioxy,
$(C_1-C_8)$-alkyloximino and
$(C_2-C_{12})$-alkanediyl,
it being possible for alkyl, alkenyl, alkanediyl, alkylidene and radicals derived therefrom, such as alkoxy, to be unbranched or branched and for one or more, preferably up to three, methylene groups to be replaced by heteroatoms/groups, such as O, $NR^{11}$ or $SiR^{12}R^{13}$ and moreover for 3 to 6 carbon atoms to form a cycle, and being optionally substituted by one or more, preferably up to three, in the case of halogen up to the maximum number, of identical or different radicals from the series halogen, halo-$(C_1-C_4)$-alkyl, $(C_3-C_8)$-cycloalkyl, $(C_1-C_8)$-acyl, phenoxy or substituted phenoxy, phenyl or substituted phenyl, $R^{11}$ being $(C_1-C_4)$-acyl and $R^{12}$ and $R^{13}$ being identical or different and independently of one another being $(C_1-C_4)$-alkyl, phenyl or substituted phenyl, $R^6$, $R^7$ and $R^8$ are independently of one another $(C_1-C_4)$-alkyl, phenyl and/or substituted phenyl, and aryl is a phenyl group which is optionally substituted by one or more, preferably up to three, identical or different groups from the series
halogen,
$(C_5-C_6)$-cycloalkyl,
phenoxy,
substituted phenoxy,
phenyl,
substituted phenyl,
$SiR^6R^7R^8$,
$O-SiR^6R^7R^8$,
$(C_1-C_{16})$-alkyl and
$(C_1-C_7)$-alkoxy,
$R^6$, $R^7$ and $R^8$ have the meaning as above;
$R^{15}$ and $R^{16}$ independently of one another are hydrogen, $(C_1-C_4)$-alkyl and/or $(C_1-C_4)$-acyl;

in $(C_1-C_6)$-acyl the hydrocarbon chain can be unbranched or branched and one or more $CH_2$ groups can be replaced by heteroatoms/groups such as O, $NR^{11}$ or $SiR^{12}R^{13}$;

$R^{11}$, $R^{12}$ and $R^{13}$ have the meaning as above; the $(C_1-C_6)$-alkyl radical with or without the above-mentioned variations (replacement of $CH_2$) can additionally be substituted by one or more, preferably up to three, identical or different groups from the series halogen, $(C_5-C_6)$-cycloalkyl, phenoxy, substituted phenoxy, phenyl and substituted phenyl; $(C_1-C_7)$-alkoxy can be unbranched or branched and one or more, preferably up to three, $CH_2$ therein can be replaced by O and moreover can be substituted by one or more, preferably up to three, in the case of halogen up to the maximum, identical or different groups from the series halogen, phenyl, substituted phenyl, $(C_5-C_6)$-cycloalkyl, phenoxy and substituted phenoxy.

The present invention relates to the compounds of the formula I in the form of the free base or of an acid addition salt. Acids which can be used for salt formation are inorganic acids, such as hydrochloric acid, hydrobromic acid, nitric acid, sulfuric acid, or phosphoric acid, or organic acids such as formic acid, acetic acid, propionic acid, malonic acid, oxalic acid, fumaric acid, adipic acid, stearic acid, oleic acid, methanesulfonic acid, benzenesulfonic acid, or toluenesulfonic acid.

The compounds of the formula 1 in some cases have one or more asymmetric carbon atoms. Racemates and diastereomers can therefore occur. The invention includes both the pure isomers and mixtures thereof. The mixtures of diastereomers can be separated into the components by customary methods, e.g. by selective crystallization from suitable solvents or by chromatography. Racemates can be separated into the enantiomers by customary methods, e.g. by salt formation with an optically active acid, separation of the diastereomeric salts and release of the pure enantiomers by means of a base.

The invention furthermore relates to a process for the preparation of compounds of the formula I, which comprises reacting compounds of the formula 2

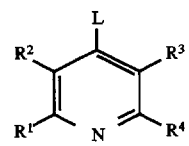

in which L is a leaving group and $R^1-R^4$ are as defined in formula 1, with appropriate amines, alcohols, phenols or mercaptans, or hydrogenating compounds of the formula 1 in which $R^1-R^4$, X and Y are as defined above and Z is an appropriately substituted unsaturated carbocyclic radical, preferably phenyl.

The substitution reaction described above is known in principle. The leaving group L can be varied within wide limits and can, for example, be a halogen atom such as fluorine, chlorine, bromine or iodine, or alkylthio such as methyl- or ethylthio, or alkanesulfonyloxy such as methane-, trifluoromethane- or ethanesulfonyloxy, or arylsulfonyloxy, such as benzenesulfonyloxy or toluenesulfonyloxy, or alkylsulfonyl such as methyl- or ethylsulfonyl, or arylsulfonyl such as phenyl- or toluenesulfonyl.

The compounds of the formula 2 can be prepared by known methods [e.g. J. Med. Chem. 32, 1970 (1989), J. Org. Chem. 29, 776 (1964), J. Prakt. Chem. 331, 369 (1989)]. Preferably those compounds 2 in which L is Cl are employed in the preparation of the compounds 1.

The reactions with alcohols and mercaptans are carried out in the presence of a strong base such as sodium hydride, potassium hydride or potassium tert-butoxide in an inert aprotic solvent such as DMF, NMP, DMSO, THF, dioxane or sulfolane at a temperature between 0° and 80° C.; in the reaction with alkoxides it can be favorable to use the accompanying alcohol as a solvent.

The conditions for the reactions of 2 with amines are dependent on the substituents $R^1$ to $R^4$ in 2 and on the structure of the amines employed; if the radicals $R^1$ to $R^4$ in 2 are inert, 2 can be reacted with an excess of amine to give 1 with or without solvent at temperatures between 80° and 200° C. The excess of amine can be reduced and the temperature lowered if acidic catalysts such as phenol [J. Amer. Chem. Soc. 73, 2623 (1951)] or salts such as triethylammonium chloride or ammonium chloride are used. Suitable solvents are e.g. DMF, N,N-dimethylacetamide, DMSO, NMP, dioxane, diethylene glycol dimethyl ether, triethylene glycol dimethyl ether, sulfolane, toluene, chlorobenzene or xylene.

Mixtures of the solvents mentioned can also be used.

If one or more radicals of $R^1$ to $R^4$ in 2 is or are an RO function, such as alkoxy and the like, poor yields of 1 or other undesired reaction products are obtained by the above-mentioned methods with amines; exceptions are the reactions with anilines and O-alkyl- or O-aralkylhydroxylamines, which lead to the products 3 and 4 (R' is the substituent of the phenyl group). Benzylamines initially yield products in with the RO function has been cleaved. These hydroxypyridines can be converted by subsequent alkylation into the compounds analogous to 3.

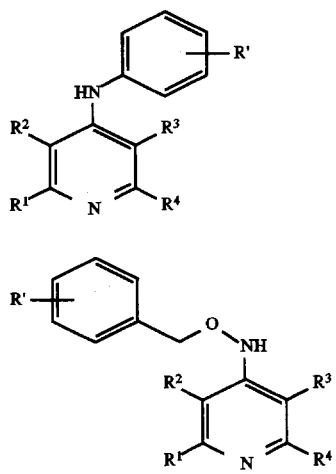

3

4

The compounds of the formula 3 can be catalytically hydrogenated to give compounds of the formula 1 (scheme 1) by known methods [e.g. F. Zymalkowski, Katalytische Hydrierungen (Catalytic Hydrogenations) p. 191, Enke Verlag, Stuttgart (1965)].

Scheme 1:

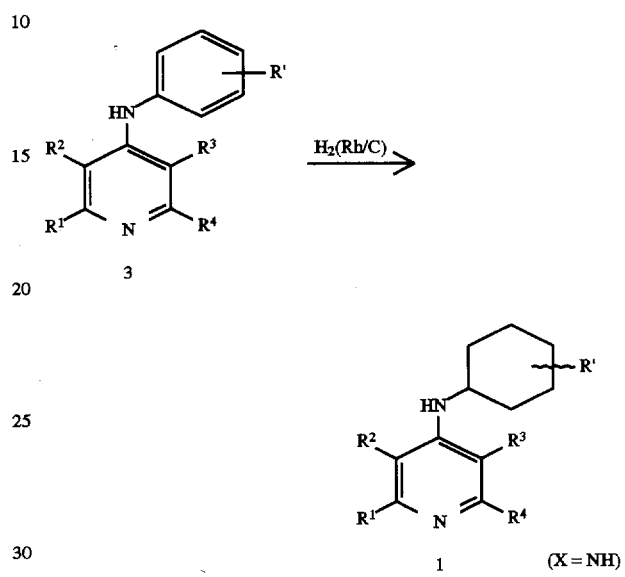

The cis/trans mixtures resulting in this way can be separated by crystallization or chromatography.

The compounds of the formula 4 are suitable intermediates for preparing a wide selection of compounds of the formula 1 where X=NH (scheme 2).

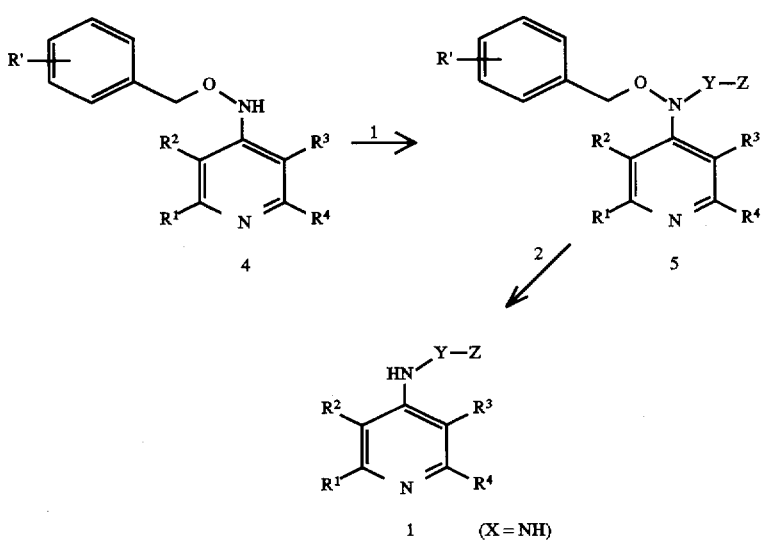

In stage 1, the products of the formula 4 are reacted selectively on the nitrogen substituent in the 4-position of the pyridine ring to give 5 using alkylating agents of the formula L—Y—Z in the presence of bases such as sodium hydride or potassium tert-butoxide; in the formula L—Y—Z L is halogen or R—SO$_3$, Y is as defined above (apart from aryl) and 2 is as indicated above. When using sterically homogeneous alkylating agents sterically homogeneous reaction products can also be obtained in this way. Solvents such as e.g. DMF, DMSO, THF, dimethoxyethane, dioxane, diethylene glycol dimethyl ether, sulfolane or toluene are employed in this reaction. Mixtures of the solvents mentioned can also be used. In stage 2 the compounds of the formula 5 are converted reductively to the compounds of the formula 1 by known methods [R. Huisgen et al. Chem. Ber. 101, 2559 (1968), C. H. Rayburn, W. R. Harlau, H. R. Haumer, Am. Soc., 1721 (1950)].

The amines, alcohols and alkylating agents employed are accessible by methods known from the literature.

The alcohols can be prepared, for example, by reduction of a carbonyl group with a suitable reductant, for example a complex metal hydride or, in the case of an aldehyde or ketone, alternatively with hydrogen and a hydrogenation catalyst. Further possibilities are the reaction of an organometallic compound with a carbonyl group or an oxirane. For the preparation of cyclohexanol derivatives, suitable substituted phenols can also be reacted with hydrogen in the presence of a hydrogenation catalyst.

The amines can, for example, be prepared by reduction of an oxime or of a nitrile with a suitable reductant, for example a complex metal hydride or hydrogen, in the presence of a hydrogenation catalyst, reductive amination or Leukart-Wallach reaction of an aldehyde or ketone or Gabriel reaction of an alkyl halide or tosylate. For the preparation of cyclohexylamine derivatives suitable substituted anilines can also be reacted with hydrogen in the presence of a hydrogenation catalyst.

The compounds of the formula 1 according to the invention are distinguished by an outstanding fungicidal action. Fungal pathogens which have already penetrated into the plant tissue can be successfully controlled in a curative manner. This is particularly important and advantageous in those fungal diseases which can no longer be effectively controlled with the otherwise customary fungicides after infection has set in. The spectrum of action of the claimed compounds includes various agriculturally important, phytopathogenic fungi, such as e.g. *Phytophthora infestans, Plasmopara viticola, Botrytis cinerea,* but also *Erysiphe graminis, Pyrenophora teres* and *Leptosphaeria nodorum.*

The compounds according to the invention are in addition also suitable for use in industrial fields, for example as wood preservatives, as preservatives in sealing compositions, in painting colors, in cooling lubricants for metal processing or as preservatives in drilling and cutting oils.

The invention also relates to compositions which contain the compounds of the formula 1 in addition to suitable formulation auxiliaries. The compositions according to the invention in general contain the active compounds of the formula 1 to 1 to 95% by weight.

They can be formulated in various ways, depending on what is prespecified by the biological and/or physicochemical parameters. Possible formulations are therefore: wettable powders (WP), emulsifiable concentrates (EC), aqueous dispersions based on oil or water (SC), suspoemulsions (SC), dusting compositions (DP), seed-dressing compositions, granules in the form of water-dispersible granules (WG), ULV formulations, microcapsules, waxes or baits.

These individual types of formulation are known in principle and are described, for example, in: Winnacker-Küchler, "Chemische Technologie" [Chemical Technology], Volume 7, C-Hauser Verlag Munich, 4th Ed. 1986; van Falkenberg, "Pesticide Formulations", Marcel Dekker New York, 2nd Ed. 1972 to 1973; K. Martens, "Spray Drying Handbook", 3rd Ed. 1979, G. Goodwin Ltd. London.

The formulation auxiliaries necessary such as inert materials, surfactants, solvents and other additives are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry, 2nd Ed., J. Wiley & Sons, New York; Marsden, "Solvents Guide", 2nd Ed., Interscience, New York 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., New York 1964; Schönfeldt, "Grenzfl ächenaktive Äthylenoxidaddukte" [Surface active ethylene oxide adducts] Wiss. Verlagsgesell., Stuttgart 1976; Winnacker-Küchler, "Chemische Technologie" [Chemical Technology], Volume 7, C-Hauser Verlag Munich, 4th Ed. 1986.

Based on these formulations, combinations with other pesticidal substances, fertilizers and/or growth regulators can also be prepared, e.g. in the form of a finished formulation or as a tank-mix.

Wettable powders are preparations which are uniformly dispersible in water, which besides the active compound and apart from a diluent or inert substance additionally contain wetting agents, e.g. polyethoxylated alkylphenols, polyethoxylated fatty alcohols, alkyl- or alkylphenolsulfonates and dispersants, e.g. sodium lignosulfonate, sodium 2,2'-dinaphthylmethane-6,6'-disulfonate, sodium dibutylnaphthalenesulfonate or alternatively sodium oleoylmethyltaurate. Emulsifiable concentrates are prepared by dissolving the active compound in an organic solvent, e.g. butanol, cyclohexanone, dimethylformamide, xylene or alternatively higher-boiling aromatics or hydrocarbons with addition of one or more emulsifiers. Examples of emulsifiers which can be used are: calcium alkylarylsulfon such as Ca dodecylbenzenesulfonate or nonionic emulsifiers such as fatty acid polyglycol esters, alkylaryl polyglycol ethers, fatty alcohol polyglycol ethers, propylene oxide-ethylene oxide-sorbitan fatty acid esters, polyoxyethylene sorbitan fatty acid esters or polyoxyethylene sorbitol esters.

Dusting compositions are obtained by grinding the active compound with finely divided solid substances, e.g. talc, natural clays such as kaolin, bentonite, poryphillite or diatomaceous earth. Granules can either be prepared by spraying the active compound onto adsorptive, granulated inert material or by applying active compound concentrates by means of adhesives, e.g. polyvinyl alcohol, sodium polyacrylate or alternatively mineral oils, to the surface of carrier substances such as sand, kaolinite or granulated inert material. Suitable active compounds can also be granulated in the manner customary for the preparation of fertilizer granules—if desired mixed with fertilizers.

In wettable powders the active compound concentration is e.g. about 10 to 90% by weight and the remainder to 100% by weight consists of customary formulation constituents. In the case of emulsifiable concentrates the active compound concentration can be about 5 to 80% by weight. Formulations in the form of dust usually contain at most 5 to 20% by weight. In the case of granules the active compound content partly depends on whether the active compound is present in liquid or solid form and which compound is present in liquid or solid form and which granulation auxiliaries, fillers etc. are used.

In addition the active compound formulations mentioned optionally contain the adhesives, wetting agents, dispersants, emulsifiers, penetrants, solvents, fillers or carriers customary in each case.

For application, the concentrates present in commercially available form are optionally diluted in a customary manner, e.g. in the case of wettable powders, emulsifiable concentrates, dispersions and in some cases also in the case of microgranules, by means of water.

Preparations in the form of dust and granulated preparations and also sprayable solutions are customarily not further diluted with other inert substances before application.

The application rate necessary varies with the external conditions such as temperature, humidity and the like. It can vary within wide limits, e.g. between 0.005 and 10.0 kg/ha or more of active substance, but it is preferably between 0.01 and 5 kg/ha.

The active compounds according to the invention can be applied, in their commercially available formulations, either on their own or in combination with other fungicides known from the literature.

Fungicides known from the literature which can be combined according to the invention with the compounds of the formula 5 and which may be mentioned are e.g. the following products:

aldimorph, andoprim, anilazine, BAS 480F, BAS 490F, benalaxyl, benodanil, benomyl, binapacryl, bitertanol, bromuconazole, buthiobate, captafol, captan, carbendazim, carboxin, CGA 173506, chlobenzthiazone, chlorthalonil, cymoxanil, cyproconazole, cyprofuram, dichlofluanid, diclomezine, diclobutrazol, diethofencarb, difenconazole (CGA 169374), difluconazole, dimethirimol, dimethomorph, diniconazole, dinocap, dithianon, dodemorph, dodine, edifenfos, ethirimol, etridiazole, fenarimol, fenfuram, fenpiclonil, fenpropidin, fenpropimorph, fentin acetate, fentin hydroxide, ferimzone (TF164), fluazinam, fluobenzimine, fluquinconazole, fluorimide, flusilazole, flutolanil, flutriafol, folpet, fosetyl-aluminum, fuberidazole, fulsulfamide (MT-F651), furalaxyl, furconazole, furmecyclox, guazatine, hexaconazole ICI ASS 04, imazalil, imibenconazole, iprobenfos, iprodione, isoprothiolane, KNF 317, copper compounds such as Cu oxychloride, oxine-Cu, Cu oxide, mancozeb, maneb, mepanipyrim (KIF 3535), metconazole, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidone, propamocarb, propiconazole, prothiocarb, pyracarbolid, pyrazophos, pyrifenox, pyroquilon, rabenzazole, RH7592, sulfur, tebuconazole, TF 167, thiabendazole, thicyofen, thiophanate-methyl, thiram, tolclofos-methyl, tolylfluanid, triadimefon, triadimenol, tricyclazole, tridemorph, triflumizole, triforine, validamycin, vinchlozolin, XRD 563, zineb, sodium dodecylsulfonate, sodium dodecylsulfate, sodium-C13/C15 alcohol ether sulfonate, sodium cetostearyl phosphate ester, dioctylsodium sulfosuccinate, sodium isopropylnaphthalenesulfonate, sodium methylenebisnaphthalenesulfonate, cetyltrimethylammonium chloride, salts of long-chain primary, secondary or tertiary amines, alkylpropyleneamines, laurylpyrimidinium bromide, ethoxylated quaternary fatty amines, alkyldimethylbenzylammoniumchloride and 1-hydroxyethyl-2-alkylimidazoline.

The abovementioned combination components are known active compounds which, for the greatest part, are described in Ch. R Worthing, U. S. B. Walker, The Pesticide Manual, 7th Edition (1983), British Crop Protection Council.

The active compound according to the invention can moreover be present mixed with other active compounds, such as insecticides, baits, sterilants, acaricides, nematicides or herbicides, in its commercially available formulations and in the application forms prepared from these formulations. The insecticides include, for example, phosphoric acid esters, carbamates, carboxylic acid esters, formamidines, tin compounds, substances prepared by microorganisms and others. Preferred mixture components are:

1. From the phosphorus compounds group acephate, azamethiphos, azinphos-ethyl, azinphos-methyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, O,O-1,2,2,2-tetrachlorethyl phosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemeton-methyl, parathion, parathionmethyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon, vamidothion.

2. From the carbamates group aldicarb, 2-sec-butylphenyl methylcarbamate (BPMG), carbaryl, carbofuran, carbosulfan, cloethocarb, benfuracarb, ethiofencarb, furathiocarb, isoprocarb, methomyl, 5-methyl-m-cumenyl butyryl(methyl)carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio-(ethylideneamino)-N-methyl-N-(morpholinothio)carbamate (UG 51717).

3. From the carboxylic acid esters group allethrin, alphamethrin, 5-benzyl-3-furylmethyl-(E)-(1R)-cis-2,2-di-methyl-3-(2-oxothiolan-3-ylidenemethyl)-cyclopropane-carboxylate, bioallethrin, bioallethrin ((S)-cyclopentyl isomer), bioresmethrin, biphenate, (RS)-1-cyano-1-(6-phenoxy-2-pyridyl)-methyl-(1RS)-trans-3-(4-tert.-butylphenyl)-2,2,-dimethylcyclopropanecarboxylate (NGI 85193), cycloprothrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D-isomer), permethrin, pheothrin ((R)-isomer), d-pralethrin, pyrethrins (natural products), resmethrin, tefluthrin, tetramethrin, tralomethrin.

4. From the amidines group amitraz, chlordimeform

5. From the tin compounds group cyhexatin, fenbutatin oxide

6. Other abamectin, Bacillus thuringiensis, bensultap, binapacryl, bromopropylate, buprofezin, camphechlor, cartap, chlorobenzilate, chlorfluazuron, 2-(4-(chlorphenyl)-4,5-diphenylthiophene (UBI-T 930), chlorfentezine, 2-naphthylmethyl cyclopropanecarboxylate (Ro12-0470), cyromazine, N-(3,5-di-chloro-4-(1,1,2,3,3,3-hexafluoro-1-propoxy)phenyl)carbamoyl)-2-chlorobenzcarboximidate, DDT, dicofol, N-(N-(3,5-dichlor-4-(1,1,2,2-tetrafluorethoxy)phenylamino)carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl)(dimethyl)(3-(3-phenoxyphenyl)propyl)silane, (4-ethoxyphenyl)(3-(4-fluoro-3-phenoxyphenyl)propyl)dimethylsilane, fenoxycarb, 2-fluoro-5-(4-(4-ethoxyphenyl-4-methyl)pentyl)diphenyl ether (MTI 800), granulosis and nuclear polyhedrosis viruses, fenthiocarb, flubenzimine, flucycloxuron, flufenoxuron, gamma-HGH, hexythiazox, hydramechylnon (AG 217300), ivermectin, 2-nitromethyl-4,5-dihydro-6H-thiazine (SD 52618), 2-nitromethyl-3,4-dihydrothiazole (SD 35651), 22-nitromethylene-1,2-thiazinon-3-ylcarbamaldehyde (WL 108477), propargite, teflubenzuron, tetradifon, tetrasul, thiocyclam, triflumuron.

The active compound content of the application forms prepared from the commercially available formulations can vary within wide ranges and the active compound concentration of the application forms can be from 0.0001 up to 95% by weight of active compound, preferably between 0.001 and 1% by weight. Application takes place in a customary manner suited to the application forms.

The active compounds have good plant compatibility and favorable toxicity to warm-blooded animals and are suitable for controlling animal pests, in particular insects, arachnids, helminthes and molluscs, very particularly preferably for controlling insects and arachnids which occur in agriculture, in animal breeding, in forestry, in storage and material protection and in the hygiene sector. They are effective against normally sensitive and resistant species and all or individual stages of development. The abovementioned pests include:

From the order of the Acarina e.g. *Acarus siro*, Agras spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp., Tetranychus spp., Eotetranychus spp., Oligonychus spp., Eutetranychus spp.

From the order of the Isopoda e.g. *Oniscus asellus, Armadillidium vulgate, Porcellio scaber.*

From the order of the Diplopoda e.g. *Blaniulus guttulatus.*

From the order of the Chilopoda e.g. *Geophilus carpophagus,* Scutigera spp.

From the order of the Symphyla e.g. *Scutigerella immaculata.*

From the order of the Thysanura e.g. *Lepisma saccharina.*

From the order of the Collembola e.g. *Onychiurus armatus.*

From the order of the Orthoptera e.g. *Blatta orientalis, Periplaneta americana, Leucophaea maderae, Blattella germanica, Acheta domesticus,* Gryllotalpa spp., *Locusta migratoria migratorioides, Melanoplus differentialis, Schistocerca gregaria.*

From the order of the Isoptera e.g. Reticulitermes spp.

From the order of the Anoplura e.g. *Phylloxera vastatrix,* Pemphigus spp., *Pediculus humanus corporis,* Haematopinus spp., Linognathus spp.

From the order of the Mallophaga e.g. Trichodectes spp., Damalinea spp.

From the order of the Thysanoptera e.g. *Hercinothrips femoralis, Thrips tabaci.*

From the order of the Heteroptera e.g. Eurygaster spp., *Dysdercus intermedius, Piesma quadrata, Cimex lectularius, Rhodnius prolixus,* Triatoma spp.

From the order of the Homoptera e.g. *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., Psylla spp.

From the order of the Lepidoptera e.g. *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana.*

From the order of the Coleoptera e.g. *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylloides chrysocephala, Epilachna varivestis,* Atomaria spp., *Oryzaephilus surinamensis,* Anthonumus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica.*

From the order of the Hymenoptera e.g. Diprion spp., Hoplocampa spp., Lasius spp., *Monomoriumpharaonis,* Vespa spp.

From the order of the Diptera e.g. Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hypobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae, Tipula paludosa.*

From the order of the Siphonaptera e.g. *Xenopsylla cheopis,* Ceratophyllus spp.

From the order of the Arachnida e.g. *Scorpio maurus, Latrodectus mactans.*

From the class of the helminths e.g. Haemonchus, Trichostrongulus, Ostertagia, Cooperia, Chabertia, Strongyloides, Oesophagostomum, Hyostrongulus, Ancylostoma, Ascaris and Heterakis and also Fasciola and plant-damaging nematodes e.g. those of the orders Meloidogyne, Heterodera, Ditylenchus, Aphelenchoides, Radopholus, Globodera, Pratylenchus, Longidorus and Xiphinema.

From the class of the gastropods, e.g. Deroceras spp., Arion spp., Lymnaea spp., Galba spp., Succinea spp., Biomphalaria spp., Bulinus epp., Oncomelania spp.

From the class of the bivalves e.g. Dreissena spp.

The invention also relates to insecticidal and acaricidal compositions which contain the compounds of the formula I in addition to suitable formulation auxiliaries.

The compositions according to the invention in general contain the active compounds of the formula 1 to 1 to 95% by weight.

They can be formulated in various ways, depending on what is prespecified by the biological and/or physicochemical parameters.

Suitable formulation possibilities are therefore:

Wettable powders (WP), emulsifiable concentrates (EC), aqueous solutions (SC), emulsions, sprayable solutions, dispersions based on oil or water (SC), suspoemulsions (SC), dusting compositions (DP), seed-dressing compositions, granules in the form of micro-, spray-, absorption and adsorption granules, water-dispersible granules (WG), ULV formulations, microcapsules, waxes or baits.

These individual types of formulation are known in principle and are described, for example, in:

Winnacker-Küchler, "Chemische Technologie" [Chemical Technology], Volume 7, C. Hauser Verlag Munich, 4th 1986; van Falkenberg "Pesticide Formulations", Marcel Dekker New York, 2nd Ed. 1972–73; K. Martens, "Spray Drying Handbook", 3rd Ed. 1979, G. Goodwin Ltd. London.

The formulation auxiliaries necessary such as inert materials, surfactants, solvents and other additives are likewise known and are described, for example, in:

Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, New York; Marsden, "Solvents Guide", 2nd Ed., Interscience, New York 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., New York 1964; Schönfeldt, "Grenzfl achenaktive Äthylenoxidaddukte" [Surface-active ethylene oxide adducts] Wiss. Verlagsgesell., Stuttgart 1976; Winnacker-Küchler, "Chemische Technologie" [Chemical Technology], Volume 7, C-Hauser Verlag Munich, 4th Ed. 1986.

Based on these formulations, combinations with other pesticidally active substances, fertilizers and/or growth regulators can also be prepared, e.g. in the form of a finished formulation or as a tank-mix. Wettable powders are preparations which are uniformly dispersible in water, which besides the active compound and apart from a diluent or inert substance additionally contain wetting agents, e.g. polyethoxylated alkylphenols, polyethoxylated fatty alcohols, alkyl- or alkylphenolsulfonates and dispersants, e.g. sodium lignosulfonate, sodium 2,2'-dinaphthylmethane-6,6'-disulfonate, sodium dibutylnaphthalenesulfonate or alternatively sodium oleoylmethyltaurate. Emulsifiable concentrates are prepared by dissolving the active compound in an organic solvent, e.g. butanol, cyclohexanone, dimethylformamide, xylene or alternatively higher-boiling aromatics or hydrocarbons with addition of one or more emulsifiers. Examples of emulsifiers which can be used are: calcium alkylarylsulfonates such as Ca dodecylbenzenesulfonate or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan fatty acid esters, polyoxyethylene sorbitan fatty acid esters or polyoxyethylene-sorbitol esters.

Dusting compositions are obtained by grinding the active compound with finely dispersed solid substances, e.g. talc, natural clays such as kaolin, bentonite, pyrophillite or diatomaceous earth. Granules can either be prepared by spraying the active compound onto adsorptive, granulated inert material or by applying active compound concentrates by means of adhesives, e.g. polyvinyl alcohol, sodium polyacrylate or alternatively mineral oils, to the surface of carrier substances such as sand, kaolinite or of granulated inert material. Suitable active compounds can also be granulated in the manner customary for the preparation of fertilizer granules—if desired mixed with fertilizers.

In wettable powders the active compound concentration is e.g. about 10 to 90% by weight and the remainder to 100% by weight consists of customary formulation constituents. In the case of emulsifiable concentrates the active compound concentration can be about 5 to 80% by weight. Formulations in the form of dust usually contain 5 to 20% by weight of active compound, sprayable solutions about 2 to 20% by weight. In the case of granules the active compound content partly depends on whether the active compound is present in liquid or solid form and which granulation auxiliaries, fillers etc., are used.

In addition the active compound formulations mentioned optionally contain the adhesives, wetting agents, dispersants, emulsifiers, penetrants, solvents, fillers or carriers customary in each case.

For application, the concentrates present in commercially available form are optionally diluted in a customary manner, e.g. in the case of wettable powders, emulsifiable concentrates, dispersions and in some cases also in the case of microgranules, by means of water. Preparations in the form of dust and granulated preparations and also sprayable solutions are customarily not further diluted with other inert substances before application.

The application rate necessary varies with the external conditions such as temperature, humidity and the like. It can vary within wide limits, e.g. between 0.001 and 10.0 kg/ha or more of active substance, but it is preferably between 0.005 and 5 kg/ha.

The active compounds according to the invention can be present in their commercially available formulations and in the application forms prepared from these formulations mixed with other active compounds, such as insecticides, baits, sterilants, acaricides, nematicides, fungicides, growth-regulating substances or herbicides.

The pesticides include, for example, phosphoric acid esters, carbamates, carboxylic acid esters, formamidines, tin compounds, substances produced by microorganisms and others.

Preferred mixture components are 1. from the phosphorus compounds group acephate, azamethiphos, azinphos-ethyl, azinphos-methyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, O,O-1,2,2,2-tetrachlorethyl phosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon, vamidothion;

2. from the carbamates group aldicarb, 2-sec-butylphenyl methylcarbamate (BPMG), carbaryl, carbofuran, carbosulfan, cloethocarb, benfuracarb, ethiofencarb, furathiocarb, isoprocarb, methomyl, 5-methyl-m-cumenyl butyryl(methyl)-carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio-(ethylideneamin)-N-methyl-N-(morpholinothio)carbamate (UG 51717);

3. from the carboxylic acid esters group allethrin, alphamethrin, 5-benzyl-3-furylmethyl-(E)-(1R)-cis-2,2-di-methyl-3-(2-oxothiolan-3-ylidenemethyl)-cyclopropane-carboxylate, bioallethrin, bioallethrin ((S)-cyclopentyl isomer), bioresmethrin, biphenate, (RS)-1-cyano-1-(6-phenoxy-2-pyridyl)-methyl-(1RS)-trans-3-(4-tert.-butylphenyl)-2,2,-dimethylcyclopropanecarboxylate (NGI 85193), cycloprothrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D-isomer), permethrin, pheothrin ((R)-isomer), d-pralethrin, pyrethrins (natural products), resmethrin, tefluthrin, tetramethrin, tralomethrin;

4. from the amidines group amitraz, chlordimeform;

5. from the tin compounds group cyhexatin, fenbutatin oxide;

6. other abamectin, Bacillus thuringiensis, bensultap, binapacryl, bromopropylate, buprofezin, camphechlor, cartap, chlorobenzilate, chlorfluazuron, 2-(4-(chlorphenyl)-4,5-diphenylthiophene (UBI-T 930), chlorfentezine, 2-naphthylmethyl cyclopropanecarboxylate (Ro12-0470), cyromazine, N-(3,5-dichloro-4-(1,1,2,3,3,3-hexafluoro-1-propoxy)phenyl)carbamoyl)-2-chlorobenzcarboximidate, DDT, dicofol, N-(N-(3,5-dichlor-4-(1,1,2,2-tetrafluorethoxy)phenylamino)carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl)(dimethyl)(3-(3-phenoxyphenyl)propyl)silane, (4-ethoxyphenyl)(3-(4-fluoro-3-phenoxyphenyl)propyl)dimethylsilane, fenoxycarb, 2-fluoro-5-(4-(4-ethoxyphenyl-4-methyl)-pentyl)diphenyl ether (MTI 800), granulosis and nuclear polyhedrosis viruses, fenthiocarb, flubenzimine, flucycloxuron, flufenoxuron, gamma-HGH, hexythiazox, hydramechylnon (AG 217300), ivermectin, 2-nitromethyl-4,5-dihydro-6H-thiazine (SD 52618), 2-nitromethyl-3,4-dihydrothiazole (SD 35651), 22-nitromethylene-1,2-thiazinon-3-ylcarbamaldehyde (WL 108477), propargite, teflubenzuron, tetradifon, tetrasul, thiocyclam, triflumuron.

The active compound content of the application forms prepared from the commercially available formulations can be from 0.00000001 up to 95% by weight of active compound, preferably between 0.00001 and 1% by weight.

Application is carried out in a customary manner suited to the application forms.

The active compounds according to the invention are also suitable for the control of endo- and ectoparasites in the veterinary medical field or in the field of animal raising.

The application of the active compounds according to the invention is carried out here in a known manner such as by oral application in the form of, for example, tablets, capsules, drinks, granules, by dermal application in the form, for example, of dipping, spraying, pouring-on and spotting-on and dusting as well as by parenteral application in the form, for example, of injection.

The novel compounds of the formula 1 according to the invention can therefore also be particularly advantageously employed in stock farming (e.g. cattle, sheep, pigs and poultry such as hens, geese etc.). In a preferred embodiment of the invention the novel compounds are administered to the animals orally, if appropriate in suitable formulations (cf. above) and if appropriate with the drinking water or feed. As excretion in the fasces takes place in an effective manner, the development of insects in the fasces of the animals can be very simply prevented in this way. The doses and formulations suitable in each case are in particular dependent on the species and the stage of development of the productive animals and also on the risk of infestation and can be easily determined and fixed by the customary methods. The novel compounds can be employed in cattle e.g. in doses of 0.01 to 1 mg/kg of body weight.

The following examples serve to illustrate the invention without the latter having to be restricted thereto.

A. CHEMICAL EXAMPLES

Example 1

4-(O-Benzylhydroxylamino)-3-methoxy-2-methylpyridine 16 g of 4-chloro-3-methoxy-2-methylpyridine, 63 g of phenol and 40 g of O-benzylhydroxylamine are stirred at 120° C. under nitrogen for 4 hours. After cooling, the mixture is shaken with 500 ml of 2N NaOH and $CH_2Cl_2$. The aqueous phase is extracted a second time with $CH_2Cl_2$. After concentrating the combined $CH_2Cl_2$ phases, excess O-benzylhydroxylamine is distilled off in vacuo at 0.6 mm. The residue crystallizes on stirring with hexane. After filtering off with suction and washing with hexane 21.6 g=88.4% of product remain. The product is recrystallized from ethyl acetate. M.p.: 130° C.

$^1$H-NMR (100 MHz, $CDCl_3$)=8.1 (d, 1H), 7.4 (s, 5H), 6.9 (d, 1H), 4.9 (s, 2H), 3.7 (s, 3H), 2.4 (s, 3H) ppm Example 2

4-[O-(4-tert-Butylbenzyl)hydroxylamino]-3-methoxy-2-methylpyridine

Prepared analogously to Example 1 from 4-chloro-3-methoxy-2-methylpyridine and O-(4-tert-butylbenzyl)hydroxylamine. Yield: 80%; m.p.: 113° C.

¹H-NMR (100 MHz, CDCl₃)=8.1 (d, 1H), 7.4 (m, 4H), 6.9 (d, 1H), 4.9 (s, 2H), 3.7 (s, 1H), 2.4 (s, 3H), 1.3 (s, 9H) ppm

Example 3

4-O-Benzylhydroxylamino-3,5-dichloropyridine

Prepared analogously to Example 1 from 3,4,5-trichloropyridine and O-benzylhydroxylamine. Yield: 78%

¹H-NMR (100 MHz, CDCl₃)=8.4 (s, 2H), 7.6 (s, 1H), 7.4 (s, 5H), 5.0 (s, 2H) ppm

Example 4

4-O-Benzylhydroxylamino-3-ethoxy-2-methylpyridine

Prepared analogously to Example 1 from 4-chloro-3-ethoxy-2-methylpyridine and O-benzylhydroxylamine. Yield: 67%

¹H-NMR (100 MHz, CDCl₃)=8.1 (d, 1H), 7.4 (s, 5H), 6.9 (d, 1H), 4.9 (s, 2H), 3.8 (q, 2H), 2.4 (s, 3H), 1.3 (t, 3H) ppm

Example 5

4-[O-Benzyl-N-(3,3-dimethyl-1,5-dioxaspiro[5.5]undec-9-yl)hydroxylamino]-3-methoxy-2-methylpyridine

Example 6

4-[O-Benzyl-N-(1,4-dioxaspiro[4.5]dec-8-yl)hydroxylamino]-3-methoxy-2-methylpyridine

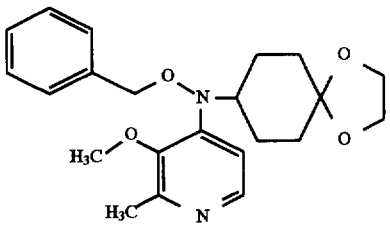

Prepared analogously to Example 5 from 4-(O-benzylhydroxylamino)-3-methoxy-2-methylpyridine and 8-tosyloxy-1,4-dioxaspiro[4.5]decane. Yield: 70%

¹H-NMR (300 MHz, CDCl₃):=8.1 (d, 1H), 7.3 to 7.4 (m, 5H), 7.1 (d, 1H), 4.7 (s, 2H), 3.9 (m, 4H), 3.8 (s, 3H), 3.6 to 3.7 (m, 1H), 2.5 (s, 3H), 1.4 to 2.1 (m, 8H) ppm

Example 7

4-[O-Benzyl-N-(4-cis-cyclohexylcyclohexyl)hydroxylamino]-3-methoxy-2-methylpyridine 7.3 g of 4-(O-benzylhydroxylamino)-3-methoxy-2-methylpyridine are added under N₂ to 4.1 g of potassium

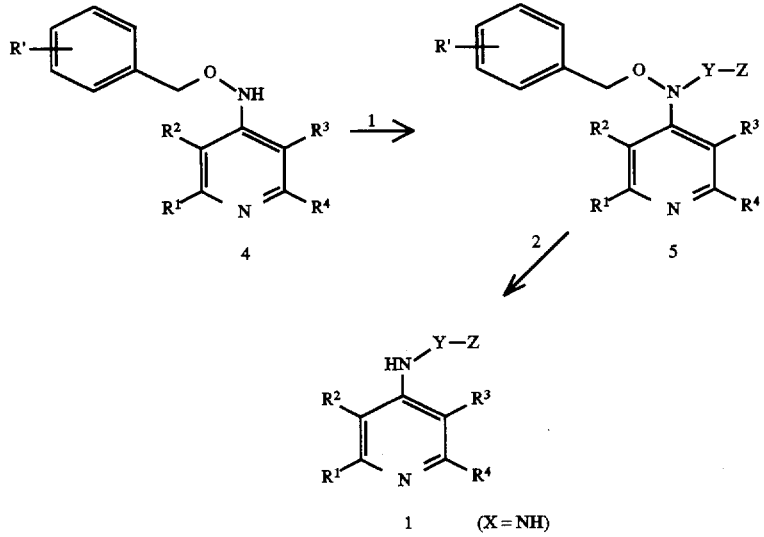

7.3 g of 4-(O-benzylhydroxylamino)-3-methoxy-2-methylpyridine in 30 ml of absolute DMSO are deprotonated under N₂ using 0.9 g of sodium hydride (80% strength). After evolution of hydrogen has ended, 11.7 g of 3,3-dimethyl-9-tosyloxy-1,5-dioxaspiro[5.5]undecane are added in 50 ml of absolute THF. The mixture is stirred at room temperature for 1 hour and at 50° C. for 4 hours. The THF is then distilled off in vacuo and the mixture is poured into water. After extracting with methylene chloride, the product is purified by chromatography on silica gel (ethyl acetate). 6.5 g=51%

¹H-NMR (100 MHz, CDCl₃)=8.1 (d, 1H), 7.3 (s, 5H), 7.1 (d, 1H), 4.7 (s, 2H), 3.8 (s, 3H), 3.5 to 3.9 (m, 1H), 3.5 (s, 4H), 2.5 (s, 3H), 1.1 to 2.4 (m, 8H), 0.9 (s, 6H) ppm tert-butoxide in 20 ml of absolute DMSO. 12.7 g of 4-trans-O-toluenesulfonylcyclohexylcyclohexane are then added dropwise and the mixture is stirred at room temperature for 17 hours and then at 50° C. for 16 hours. After cooling, the THF is distilled off in vacuo and the mixture is poured into water. After extracting several times with ethyl acetate, the product is isolated by column chromatography (silica gel; ethyl acetate/hexane 1:1). 8.6 g=70.2%

¹H-NMR (100 MHz, CDCl₃)=8.1 (d, 1H), 7.4 (s, 5H), 7.1 (d, 1H), 4.7 (s, 2H), 3.8 (s, 3H), 3.5 to 3.9 (m, 1H), 2.5 (s, 3H), 0.6 to 2.0 (m, 20H) ppm

Example 8

4-[O-Benzyl-N-(4-cis-[1,1,3,3-tetramethylbut-1-yl]
cyclohexyl)hydroxylamino]-3-methoxy-2-
methylpyridine hydrochloride Prepared analogously to Example 7 from 4-(O-benzylhydroxylamino)-3-methoxy-2-methylpyridine and trans-1-(4-toluenesulfonyloxy)-4-(1,1,3,3-tetramethylbutyl) cyclohexane. Yield: 30%

$^1$H-NMR (100 MHz, CDCl$_3$)=8.1 (t, 1H), 7.4 (s, 5H), 7.4 to 7.5 (d, 1H), 4.8 (s, 2H), 4.2 to 4.4 (m, 1H), 3.8 (s, 3H), 2.8 (s, 3H), 1.2 to 2.0 (m, 9H), 1.2 (s, 2H), 0.9 and 0.8 (2s, 15H) ppm

Example 9

4-[O-Benzyl-N-(4-trans-1,1,3,3-tetramethylbut-1-yl
-cyclohexyl)-hydroxylamino]-3-methoxy-2-
methylpyridine hydrochloride Prepared analogously to Example 7 from 4-(O-benzylhydroxylamino)-3-methoxy-2-methylpyridine and cis-1-(4-toluenesulfonyloxy)-4-(1,1,3,3-tetramethylbutyl) cyclohexane. Yield: 53%.

$^1$H-NMR (100 MHz, CDCl$_3$)=8.0 (t, 1H), 7.4 (s, 5H), 7.2 to 7.4 (d, 1H), 4.8 (s, 2H), 3.9 to 4.2 (m, 1H), 3.5 (s, 3H), 2.8 (s, 3H), 0.8 to 2.0 (m, 9H), 1.2 (s, 2H), 0.9 and 1.0 (2s, 15H), ppm

Example 10

4-[O-Benzyl-N-(cis-decalin-2-yl)hydroxylamino]-3-
methoxy-2-methylpyridine

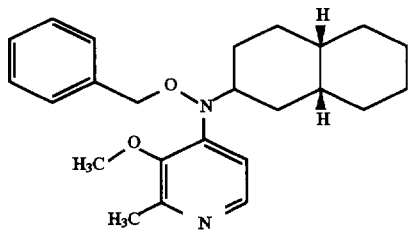

Prepared analogously to Example 7 from 4-(O-benzylhydroxylamino)-3-methoxy-2-methylpyridine and 2-(4-toluenesulfonyloxy)cis-decalin. Yield: 21%

$^1$H-NMR (100 MHz, CDCl$_3$)=8.1 (d, 2H), 7.4 (s, 5H), 7.1 (d, 1H), 4.7 (s, 2H), 4.8 (s, 3H), 3.7 to 4.0 (m, 1H), 2.5 (s, 3H), 1.1 to 2.1 (m, 16H), ppm

Example 11

4-[O-Benzyl-N-(4-cis-phenylcyclohexyl)
hydroxylamino]-3-methoxy-2-methylpyridine
hydrochloride Prepared analogously to Example 7 from 4-(O-benzylhydroxylamino)-3-methoxy-2-methylpyridine and trans-1-(4-toluenesulfonyloxy)-4-phenylcyclohexane. Yield: 38%

$^1$H-NMR (100 MHz, CDCl$_3$)=8.3 (d, 1H), 7.4 (d, 1H), 7.2 and 7.3 (2s, 10H), 6.4 to 6.7 (m, 1H), 4.8 (s, 2H), 4.2 to 4.4 (m, 1H), 3.8 (s, 3H), 2.6 (s, 3H), 1.4 to 3.0 (m, 9H) ppm

Example 12

4-[O-Benzyl-N-(4-cis-[1,1-dimethylpropyl-1]
cyclohexyl)hydroxylamino]-3-ethoxy-2-
methylpyridine hydrochloride Prepared analogously to Example 7 from 4-(O-benzylhydroxylamino)-3-ethoxy-2-methylpyridine and trans-1-(4-toluenesulfonyloxy)-4-(1,1-dimethylprop-1-yl) cyclohexane. Yield: 50%

$^1$H-NMR (100 MHz, CDCl$_3$)=8.1 (d, 1H), 7.5 (d, 1H), 7.3 (d, 1H), 4.8 (s, 2H), 4.3 to 4.5 (m, 1H), 4.0 (q, 2H), 2.8 (s, 3H), 1.4 (t, 3H), 1.0 to 2.1 (m, 11H), 0.6 to 0.8 (t and s, 9H) ppm

Example 13

4-[O-Benzyl-N-(4-cis-[4-ethoxyphenyl]cyclohexyl)
hydroxylamino]-3-methoxy-2-methylpyridine Prepared analogously to Example 7 from 4-(O-benzylhydroxylamino)-3-methoxy-2-methylpyridine and trans-1-(4-toluenesulfonyloxy)-4-(4-ethoxyphenyl) cyclohexane. Yield: 32%

$^1$H-NMR (100 MHz, CDCl$_3$)=8.1 (d, 1H), 7.1 to 7.4 (m, 9H), 6.8 (d, 1H), 4.6 (s, 2H), 4.0 (q, 2H), 3.8 (s, 3H), 2.5 (s, 3H), 1.5 (t, 3H), 1.3 to 2.9 (m, 9H) ppm

Example 14

4-[O-Benzyl-N-(4-cis-tert-amylcyclohexyl)
hydroxylamino]-3-methoxy-2-methylpyridine
hydrochloride Prepared analogously to Example 7 from 4-(O-benzylhydroxy)-3-methoxy-2-methylpyridine and trans-1-tosyloxy-4-tert-amylcyclohexane. Yield: 45%

$^1$H-NMR (100 MHz, CDCl$_3$)=8.3 (t, 1H), 7.5 (d, 1H), 7.4 (m, 5H), 4.8 (s, 2H), 4.5 (m, 1H), 3.8 (s, 1H), 2.4 (s, 3H), 0.8 to 2.1 (m, 20H) ppm

Example 15

4-(3,3-Dimethyl-1,5-dioxaspiro[5.5]undec-9-
ylamino)-3-methoxy-2-methylpyridine

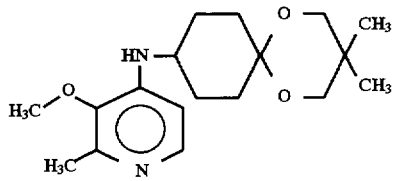

6.5 g of 4-[O-benzyl-N-(3,3-dimethyl-1,5-dioxaspiro[5.5] undec-9-yl)hydroxylamino]-3-methoxy-2-methylpyridine in 70 ml of methanol are hydrogenated using 2 g of Raney nickel at normal pressure until absorption of hydrogen is complete. After filtering, the filtrate is concentrated and the product is dissolved in diisopropyl ether. Crystallization takes place on addition of hexane. 4.3 g=90%; m.p.: 45° C.

$^1$H-NMR (100 MHz, CDCl$_3$)=7.9 (d, 1H), 6.4 (d, 1H), 4.5 (d, 1H), 3.7 (s, 3H), 3.5 (m, 4H), 3.3 to 3.5 (m, 1H), 2.4 (s, 3H), 1.4 to 2.4 (m, 8H), 1.0 (s, 6H) ppm

Example 16

4-(1,4-Dioxaspiro[4.5]dec-8-ylamino)-3-methoxy-2-methylpyridine hydrochloride

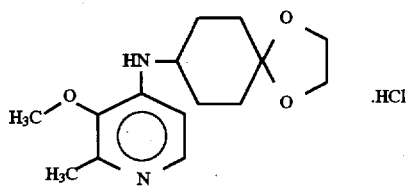

27.3 g of 4-[O-benzyl-N-(1,4-dioxaspiro[4.5]dec-8-yl)hydroxylamino]-3-methoxy-2-methylpyridine are hydrogenated as described above. After filtering and concentrating, the product is dissolved in methylene chloride and the hydrochloride is formed with ethereal HCl. After concentrating, the residue is stirred with hexane, filtered off with suction and washed several times with hexane. 21 g=93%

$^1$H-NMR (100 MHz, CDCl$_3$)=7.9 (d, 1H), 6.4 (d, 1H), 4.5 (d, 1H), 4.0 (s, 4H), 3.7 (s, 3H), 3.1 to 3.4 (m, 1H), 2.4 (s, 3H), 1.4 to 2.1 (m, 8H) ppm

Example 17

4-[4-cis-(4-Ethoxyphenyl)cyclohexylamino]-3-methoxy-2-methylpyridine

Prepared analogously to Example 15 from 4-[O-benzyl-N-(4-cis-[4-ethoxyphenyl]cyclohexyl)hydroxylamino]-3-methoxy-2-methylpyridine. Yield: 91%

$^1$H-NMR (100 MHz, CDCl$_3$)=8.0 (d, 1H), 7.0 (q, 4H), 6.4 (d, 1H), 4.9 (d, 1H), 4.0 (q, 2H), 3.8 (s, 3H), 3.6 to 3.8 (m, 1H), 2.4 (s, 3H), 1.6 to 2.8 (m, 9H) 1.4 (t, 3H) ppm

Example 18

4-(4-cis-Phenylcyclohexylamino)-3-methoxy-2-methylpyridine hydrochloride

Prepared analogously to Example 16 from 4-[O-benzyl-N-(4-cis-phenylcyclohexyl)hydroxylamino]-3-methoxy-2-methylpyridine. Yield: 90%; M.p.: 175° C.

$^1$H-NMR (100 MHz, CDCl$_3$)=8.0 (t, 1H), 7.2 (s, 5H), 6.7 (d, 1H), 5.9 (d, 1H), 3.9 (s, 3H), 3.8 to 4.0 (m, 1H), 2.7 (s, 3H), 1.5 to 2.6 (m, 9H)

Example 19

4-(4-cis-Cyclohexylcyclohexylamino)-3-methoxy-2-methylpyridine hydrochloride

Prepared analogously to Example 16 from 4-[O-benzyl-N-(4-cis-cyclohexylcyclohexyl)hydroxylamino]-3-methoxy-2-methylpyridine. Yield: 96%

$^1$H-NMR (100 MHz, CDCl$_3$)=8.0 (t, 1H), 6.6 (d, 1H), 3.8 (s, 3H), 3.7 to 3.9 (m, 1H), 2.7 (s, 3H), 0.8 to 1.9 (m, 20H) ppm

Example 20

4-(4-cis-tert-Amylcyclohexylamino)-3-methoxy-2-methylpyridine

Prepared analogously to Example 15 from 4-[O-benzyl-N-(4-cis-tert-amylcyclohexyl)hydroxylamino]-3-methoxy-2-methylpyridine. Yield: 69%

$^1$H-NMR (100 MHz, CDCl$_3$)=7.9 (d, 1H), 6.4 (d, 1H), 4.8 (d, 1H), 3.7 (s, 3H), 3.7 (m, 1H), 2.3 (s, 3H), 0.7 to 2.1 (m, 20H) ppm

Example 21

4-(cis-Decalin-2-ylamino)-3-methoxy-2-methylpyridine hydrochloride

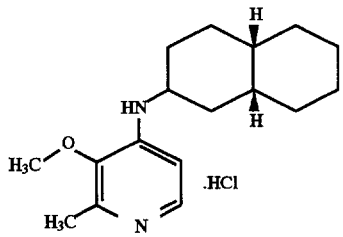

Prepared analogously to Example 16 from 4-[O-benzyl-N-(cis-decalin-2-yl)hydroxylamino]-3-methoxy-2-methylpyridine. Yield: 70%

$^1$H-NMR (100 MHz, CDCl$_3$)=7.9 (t, 1H), 6.6 (d, 1H), 3.8 (s, 3H), 3.5 to 3.8 (m, 1H), 2.7 (s, 3H), 0.7 to 2.2 (m, 16H) ppm

Example 22

4-[4-cis-(1,1,3,3-Tetramethylbutyl)cyclohexylamino]-3-methoxy-2-methylpyridine hydrochloride Prepared analogously to Example 16 from 4-[O-benzyl-N-(4-cis-[1,1,3,3-tetramethylbutyl]cyclohexyl)hydroxylamino]-3-methoxy-2-methylpyridine. Yield: 76%

$^1$H-NMR (100 MHz, CDCl$_3$)=8.0 (t, 1H), 6.7 (d, 1H), 3.8 (s, 3H), 3.8 to 3.9 (s, 1H), 2.7 (s, 3H), 1.0 to 2.1 (m, 11H), 0.9 (2s, 15H) ppm

Example 23

4-[4-trans-(1,1,3,3-Tetramethylbutyl)cyclohexylamino]-3-methoxy-2-methylpyridine hydrochloride Prepared analogously to Example 16 from 4-[O-benzyl-N-(4-trans-[1,1,3,3-tetramethylbutyl]cyclohexyl)hydroxylamino]-3-methoxy-2-methylpyridine. Yield: 80%

$^1$H-NMR (100 MHz, CDCl$_3$)=7.9 (t, 1H), 6.6 (d, 1H), 3.8 (s, 3H), 3.2 to 3.5 (m, 1H), 2.7 (s, 3H), 1.0 to 2.3 (m, 11H), 0.9 (2s, 15H) ppm

Example 24

4-(4-cis-tert-Amylcyclohexylamino)-3-ethoxy-2-methylpyridine

Prepared analogously to Example 15 from 4-[O-benzyl-N-(4-cis-tert-amylcyclohexyl)hydroxylamino]-3-ethoxy-2-methylpyridine. Yield: 49%

$^1$H-NMR (100 MHz, CDCl$_3$)=7.9 (d, 1H), 6.3 (d, 1H), 4.8 (d, 1H), 3.8 (q, 2H), 3.6 (m, 1H), 2.3 (s, 3H), 1.4 (t, 3H), 0.8 (s, t, 9H), 0.6–2.0 (m, 11H) ppm

Example 25

4-(4-Oxocyclohexylamino)-3-methoxy-2-methylpyridine hydrochloride 27.3 g of 4-(1,4-dioxaspiro[4.5]dec-8-ylamino)-3-methoxy-2-methylpyridine hydrochloride are stirred with 400 ml of formic acid for 4 hours. The residue which remains after concentrating in vacuo is dissolved in methylene chloride and shaken with 2N NaOH. The methylene chloride phase is concentrated, the residue is dissolved in ether and the hydrochloride is precipitated by addition of ethereal HCl. 14 g=90%; m.p.: 115° to 120° C.

$^1$H-NMR (100 MHz, CDCl$_3$)=8.0 (d, 1H), 7.0 (d, 1H), 6.2 (d, 1H), 4.0 to 4.3 (m, 1H), 3.8 (s, 3H), 2.6 (s, 3H), 1.8 to 2.7 (m, 8H) ppm

Example 26

4-[4-(O-Benzyloximino)cyclohexylamino]-3-methoxy-2-methylpyridine 2 g of 4-(4-oxocyclohexylamino)-3-methoxy-2-methylpyridine and 1.2 g O-benzylhydroxylamine are boiled in toluene in a water separator until liberation of water has ended. The product is isolated by column chromatography (ethyl acetate/methanol 9:1; silica gel). 1.8 g=53%

$^1$H-NMR (100 MHz, CDCl$_3$)=8.0 (d, 1H), 7.4 (s, 5H), 6.4 (d, 1H), 5.1 (s, 2H), 4.6 (d, 1H), 3.7 (s, 3H), 3.0 to 3.7 (m, 2H), 2.4 (s, 3H), 1.3 to 2.5 (m, 7H) ppm

Example 27

4-(4-Benzylidenecyclohexylamino)-3-methoxy-2-methylpyridine

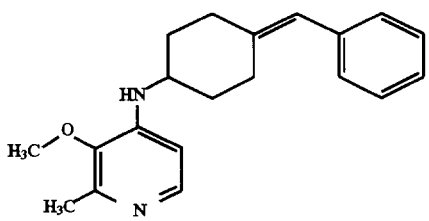

7.8 g of benzyltriphenylphosphonium bromide in 50 ml of ethylene glycol dimethyl ether are deprotonated at 10° to 20° C. using 11 ml of 1.6 molar butyllithium solution in hexane. After 30 minutes 1.3 g of 4-(4-oxocyclohexylamino)-3-methoxy-2-methylpyridine are added dropwise in 10 ml of DMSO. After 5 hours at 40° to 50° C. the mixture is poured into water and extracted with methylene chloride. The product is purified by column chromatography on silica gel (eluent: ethanol). 0.6=41%; m.p.: 120° C.

$^1$H-NMR (100 MHz, CDCl$_3$)=8.0 (d, 1H), 7.2 (m, 5H), 6.4 (d, 1H), 6.3 (s, 1H), 4.6 (d, 1H), 3.7 (s, 3H), 3.4 to 3.8 (m, 1H), 2.4 (s, 3H), 1.2 to 3.0 (m, 8H) ppm

Example 28

4-[4-(4-tert-Butylbenzyl)cyclohex-3-en-1-ylamino]-3-methoxy-2-methylpyridine 1.2 g of 4-[(4-hydroxy-4-tert-butylbenzyl)cyclohexylamino]-3-methoxy-2-methylpyridine in 40 ml of toluene are heated to 80° C. for 4 hours with 1.1 g of para-toluenesulfonic acid. The mixture is then poured into NaHCO$_3$ solution and the toluene phase is separated. The product which remains after concentrating the toluene is purified via the hydrochloride. Yield: 53%

$^1$H-NMR (100 MHz, CDCl$_3$)=7.9 (d, 1H), 7.0 to 7.4 (m, 4H), 6.4 (d, 1H), 5.4 (m, 1H), 4.6 (d, 1H), 3.6 (s, 3H) ppm

Example 29

4-(4-Hydroxy-4-tert-butylbenzylcyclohexylamino)-3-methoxy-2-methylpyridine

Isomer mixture

A Grignard solution is prepared from 1.2 g of magnesium and 12.9 g of 90% strength 4-tert-butylbenzyl bromide in 100 ml of abs. ether. 2.9 g of 4-(4-oxocyclohexylamino)-3-methoxy-2-methylpyridine in 50 ml of absolute THF are added dropwise to this solution. After 17 hours at room temperature it is acidified with 25 ml of 2N HCl, the mixture is extracted several times with ethyl acetate and the combined ethyl acetate phases are washed with sodium hydrogen carbonate solution. Purification is carried out by column chromatography on silica gel using ethyl acetate to which increasing amounts of methanol are added.

Isomer 1: 0.6 g=13%, isomer mixture: 1.8 g=39%,

Isomer 2: 2.1 g=22%

Isomer 1:

$^1$H-NMR (100 MHz, CDCl$_3$)=7.9 (d, 1H), 7.1 to 7.3 (m, 4H), 6.4 (d, 1H), 4.5 (d, 1H), 3.6 (s, 3H), 3.1 to 3.3 (m, 1H), 2.7 (s, 2H), 2.4 (s, 3H), 1.4–2.0 (m, 8H), 1.3 (s, 9H) ppm Isomer 2:

$^1$H-NMR (100 MHz, CDCl$_3$)=7.9 (d, 1H), 7.1 to 7.3 (m, 4H), 6.4 (d, 1H), 4.6 (d, 1H), 3.6 (s, 3H), 3.4 to 3.6 (m, 1H), 2.8 (s, 2H), 2.4 (s, 3H), 1.5 to 2.2 (m, 8H), 1.3 (s, 9H) ppm

Example 30

4-[(4-Hydroxy-4-n-octyl)cyclohexylamino]-3-methoxy-2-methylpyridine

The Grignard solution is prepared from 0.73 g of magnesium and 6.0 g of octyl bromide in 50 ml of absolute THF. 2.8 g of 4-(4-oxocyclohexylamino)-3-methoxy-2-methylpyridine in 20 ml of THF are added dropwise to the solution. After 2 hours the mixture is acidified with 2N HCl. The THF is then distilled off in vacuo at room temperature and the product is extracted from the solution which is rendered alkaline with methylene chloride. Further working up takes place as in the previous working procedure.

| Yield: | Isomer 1: | 0.4 g = 10% |
|---|---|---|
| | Mixed fraction: | 0.7 g = 17% |
| | Isomer 2: | 0.2 g = 5% |

Isomer 1:

$^1$H-NMR (100 MHz, CDCl$_3$)=7.9 (d, 1H), 6.4 (d, 1H), 4.5 (d, 1H), 3.7 (s, 3H), 3.2 (m, 1H), 2.4 (s, 3H), 1.2 to 2.0 (m, 22H), 0.9 (t, 3H) ppm Isomer 2: $^1$H-NMR (100 MHz, CDCl$_3$)=7.9 (d, 1H), 6.4 (d, 1H), 4.6 (d, 1H), 3.7 (s, 3H), 3.5 (m, 1H), 2.4 (s, 3H), 1.2 to 2.1 (m, 22H), 0.9 (t, 3H) ppm

Example 31

4-[4-(4-tert-Butylanilino)cyclohexylamino-3-methoxy-2-methylpyridine 2.3 g of 4-(4-oxocyclohexylamino)-3-methoxy-2-methylpyridine, 1.5 g of 4-tert-butylaniline, 0.6 g of glacial acetic acid and 3.2 g of sodium triacetoxyborohydride are stirred in 20 ml of dichloroethane for 24 hours. The mixture is then acidified with 2N HCl and the dichloroethane is removed in vacuo. It is then rendered alkaline with 2N NaOH and extracted several times with ethyl acetate. The combined extracts are concentrated and the residue is crystallized using ether. The isomer mixture is filtered off with suction and dried. 3.5 g=96%

$^1$H-NMR (100 MHz, CDCl$_3$)=8.0 (d, 1H), 7.2 and 6.6 (2m, 5H), 5.5 and 5.7 (2d, 1H), 3.8 (2s, 3H), 3.2 to 3.7 (m, 2H), 2.6 (s, 3H), 1.1 to 2.3 (m, 17H) ppm

Example 32

4-[4-(4-cis-tert-Butylcyclohexylamino) cyclohexylamino]-3-methoxy-2-methylpyridine

Isomer mixture hydrochloride

Analogously to Example 31, prepared from 4-(4-oxocyclohexylamino)-3-methoxy-2-methylpyridine and cis-4-tert-butylcyclohexylamine. Purification is carried out via the hydrochloride. Yield: 92%

$^1$H-NMR (100 MHz, DMSO d-6)=8.0 (2d, 1H), 7.0 (2d, 1H), 3.9 to 3.1 (4m, 3H), 3.7 and 3.8 (2s, 3H), 2.5 (s, 3H), 1.0 to 2.3 (m, 17H), 0.9 (s, 9H) ppm

Example 33

4-(4-tert-Butylanilino)-3-methoxy-2-methylpyridine

7.9 g of 4-chloro-3-methoxy-2-methylpyridine and 22.4 g of 4-tert-butylaniline are heated at 120° C. for 8 hours in 20 g of phenol. After cooling, the mixture is poured into NaOH and the product is extracted using methylene chloride. After concentrating, the excess of amine is distilled off in vacuo and the residue is crystallized using hexane. 9.5 g=55%

$^1$H-NMR (100 MHz, CDCl$_3$)=8.0 (d, 1H), 7.0 to 7.4 (m, 4H), 6.9 (d, 1H), 3.8 (s, 3H), 2.5 (s, 3H), 1.3 (s, 9H) ppm

Example 34

4-(4-tert-Butylcyclohexylamino)-3-methoxy-2-methylpyridine cis/trans mixture

1 g of 4-(4-tert-butylanilino)-3-methoxy-2-methylpyridine in 20 ml of methanol, 3.7 ml of 2N HCl and 1.3 ml of water are hydrogenated at room temperature and normal pressure until absorption of hydrogen has ended using 1 g of rhodium on alumina (5% strength). After filtering and concentrating 1 g of syrup remains=100% isomer mixture.

The isomer ratio was determined by means of HPLC. It is 60:40 cis/trans.

Using rhodium on carbon (5% strength) an isomer ratio of 66:34 cis/trans is achieved.

| Column: | Chiracel OD (Daicel), 250 × 4.0 mm |
|---|---|
| Precolumn: | 5.0 × 4.0 mm |
| Eluent: | n-Hexane/2-propanol 9:1 containing 0.1% diethylamine |
| Flow rate: | 1.0 ml/min |
| Detection: | UV/250.4 nm |

The cis isomer appears after 5.2 minutes, the trans-isomer after 7.2 minutes.

Example 35

4-(3-cis-tert-Amylcyclopentylamino)-3-chloro-2-methylpyridine

1.2 g of 3,4-dichloro-2-methylpyridine and 1.5 g of 3-tert-amylcyclopentylamine are heated at 180° C. for 4 hours with 60 mg of ammonium chloride in 5 ml of N-methylpyrrolidone. After addition of 0.3 g of 3-tert-amylcyclopentylamine, the mixture was heated for a further 2 hours. After cooling it was poured into 30 ml of saturated sodium bicarbonate solution and extracted with 70 ml of ethyl acetate. The organic phase was washed twice using 20 ml of water each time. After drying and concentrating the ethyl acetate phase 5.3 g of crude product remained. The syrup was chromatographed on silica gel using ethyl acetate/heptane 4:1. The still not quite pure product is chromatographed a second time, this time on Sephadex using methanol. Yield: 1.3 g=61%

$^1$H-NMR (100 MHz, CDCl$_3$)=8.0 (d, 1H), 6.4 (d, 1H), 4.8 (d, 1H), 3.8 (m, 1H), 2.5 (s, 3H), 0.7 to 2.3 (m, 18H) ppm

Example 36

4-[4-cis-(1,1,3,3-Tetramethylbutyl)cyclohexylamino]-3-chloro-2-methylpyridine

Preparation was carried out analogously to Example 35 from 3,4-dichloro-2-methylpyridine and 4-(1,1,3,3-tetramethylbutyl)cyclohexylamine (cis/trans mixture). Separation of the isomers was carried out by chromatography on silica gel using EA/heptane 1:1 and EA/heptane 2:1. Yield: 21% cis-isomer 21% trans-isomer $^1$H-NMR (100 MHz, CD$_3$OD) cis-isomer=7.9 (d, 1H), 6.6 (d, 1H), 3.8 (m, 1H), 2.5 (s, 3H), 1.0 (2s, 15H), 1.1 to 2.1 (m, 11H) ppm $^1$H-NMR (100 MHz, CD$_3$OD) trans-isomer=7.9 (d, 1H), 6.6 (d, 1H), 3.4 (m, 1H), 2.5 (s, 3H), 1.0 (2s, 15H), 1.1 to 2.2 (m, 11H) ppm

Example 37

4-[N-(4-Fluorophenyl)piperidin-4-ylamino]-3-chloro-2-methylpyridine

Analogously to Example 35 from 3,4-dichloro-2-methylpyridine and 4-amino-N-(4-fluorophenyl)piperidine. Reaction time: 8 hours. Purification was carried out by chromatography on silica gel using EA/heptane 1:1, EA/heptane 4:1 and EA/methanol 19:1. The product was purified further by chromatography on Sephadex using methanol. Yield 31%

$^1$H-NMR (300 MHz, CDCl$_3$)=8.0 (d, 1H), 6.9 to 7.0 (m, 4H), 6.4 (d, 1H), 4.8 (d, 1H), 3.5 (m, 3H), 2.9 (m, 2H), 2.5 (s, 3H), 2.1 to 2.2 (m, 2H), 1.6 to 1.8 (m, 2H) ppm

Example 38

4-[2-(2,3-Dimethyl-4-(methoxyethyl)phenoxy) ethylamino]-3-chloro-2-methylpyridine

Preparation was carried out analogously to Example 35 from 3,4-dichloro-2-methylpyridine. The mixture was heated for 6 hours and purified on silica gel using ethyl acetate, then on Sephadex using methanol. Yield: 19%

$^1$H-NMR (100 MHz, CDCl$_3$)=8.1 (d, 1H), 6.8 (q, 2H), 6.5 (d, 1H), 5.3 (t, 1H), 4.2 (t, 2H), 3.4 to 3.7 (2t, 4H), 3.3 (s, 3H), 3.9 (s, 3H), 2.2 (2s, 6H) ppm

Example 39

4-[4-(4-(3,6-Dioxaoctyloxy)-phenyl) cyclohexylamino]-3-chloro-2-methylpyridine

Preparation was carried out analogously to Example 35 from 3,4-dichloro-2-methylpyridine and 4-(4-(3,6-dioxaoctyloxy)phenyl)cyclohexylamine. After 4.5 hours the mixture is worked up. Yield: 28%

$^1$H-NMR (300 MHz, CDCl$_3$)=8.1 (d, 1H), 6.8 to 7.2 (m, 4H), 6.5 (d, 1H), 5.2 (d, 1H), 3.5 to 4.2 (m, 11H), 2.6 (s, 3H), 1.2 (t, 3H), 1.6 to 2.2 (m, 9H) ppm

Example 40

3-Chloro-4-[2-(2,4-dimethylphenoxy)propylamino]-2-methylpyridine

Analogously to Example 35 from 3,4-dichloropyridine and 2-(2,4-dimethylphenoxy)propylamine. After 2 hours at 180° C. the mixture was worked up. Yield: 63%

$^1$H-NMR (100 MHz, CD$_2$OD)=7.9 (d, 1H), 6.9 to 7.0 (m, 3H), 6.7 (d, 1H), 4.6 (m, 1H), 3.5 (m, 2H), 2.5 (s, 3H), 2.2 (s, 3H), 2.1 (s, 3H), 1.3 (d, 3H) ppm

Example 41

4-[4-(3-Cyclohexylpropylidene)cyclohexylamino]-3-ethoxy-2-methylpyridine

Preparation was carried out analogously to Example 27 from 4-(4-oxocyclohexylamino)-3-ethoxy-2-methylpyridine and 3-cyclohexylpropyltriphenylphosphonium chloride. Yield: 42%

$^1$H-NMR (100 MHz, CDCl$_3$)=8.0 (d, 1H), 6.4 (d, 1H), 5.1 (t, 1H), 4.5 (d, 1H), 3.9 (q, 2H), 3.5 (m, 1H), 2.4 (s, 3H), 1.4 (t, 3H), 0.7 to 2.2 (m, 23H) ppm

Example 42

4-(4-Undecylidenecyclohexylamino)-3-ethoxy-2-methylpyridine

Preparation was carried out analogously to Example 27 from 4-(4-oxocyclohexylamino)-3-ethoxy-2-methylpyridine and undecyl triphenylphosphonium bromide. Yield: 51%

$^1$H-NMR (100 MHz, CDCl$_3$)=7.9 (d, 1H), 6.4 (d, 1H), 5.2 (t, 1H), 4.5 (d, 1H), 3.8 (q, 2H), 3.4 (m, 1H), 2.4 (s, 3H), 1.4 (t, 3H), 0.9 (t, 3H), 1.0 to 2.3 (m, 26H) ppm

Example 43

4-(4-cis-Phenylcyclohexyloxy)-3-methoxy-2-methylpyridine 1.9 g of 4-cis-phenylcyclohexanol in 20 ml of absolute DMSO are stirred at 40° to 50° C. with 330 mg of 80% strength sodium hydride until evolution of hydrogen has ended. 1.6 g of 4-chloro-3-methoxy-2-methylpyridine are then added to the solution and it is stirred at 100° C. for 16 hours. After cooling, the mixture is poured into water and extracted with ethyl acetate. Column chromatography on silica gel using ethyl acetate yields 1.7 g=57% of product. M.p.: 89° to 90° C.

$^1$H-NMR (100 MHz, CDCl$_3$)=8.1 (d, 1H), 7.2 (m, 5H), 6.7 (d, 1H), 4.4 (m, 1H), 3.9 (s, 3H), 2.5 (s, 3H), 1.5 to 2.9 (m, 9H) ppm

Example 44

4-[4-cis-(1,1-Dimethylprop-1-yl)cyclohexyloxy]-3-methoxy-2-methylpyridine

Preparation was carried out analogously to Example 43 from 4-chloro-3-methoxy-2-methylpyridine and 4-cis-(1,1-dimethylprop-1-yl)cyclohexanol. Yield: 52%

$^1$H-NMR (100 MHz, CDCl$_3$)=8.0 (d, 1H), 6.7 (d, 1H), 4.2 (m, 1H), 3.8 (s, 3H), 2.4 (s, 3H), 0.7 to 2.3 (m, 20H) ppm

Example 45

4-(3,3-Dimethyl-1,5-dioxaspiro[5.5]undecan-9-yloxy)-3-methoxy-2-methylpyridine

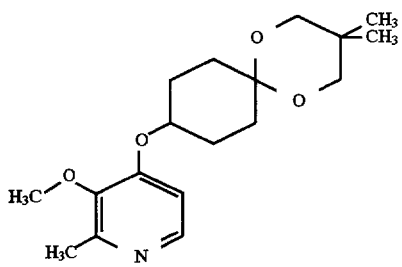

Preparation was carried out analogously to Example 43 from 4-chloro-3-methoxy-2-methylpyridine and 3,3-dimethyl-1,5-dioxaspiro[5.5]undecan-9-ol. Yield: 75%; M.p.: 90° C.

$^1$H-NMR (100 MHz, CDCl$_3$)=8.1 (d, 1H), 6.7 (d, 1H), 4.5 (m, 1H), 3.8 (s, 3H), 3.5 (d, 4H), 2.5 (s, 3H), 1.9 (m, 8H), 1.0 (s, 6H) ppm

Example 46

[(1S)-endo-Bornyl]-3-methoxy-2-methylpyridine

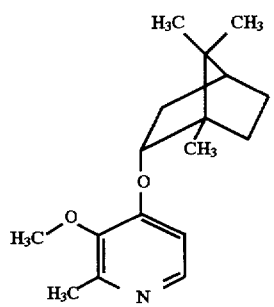

Preparation was carried out analogously to Example 43 from 4-chloro-3-methoxy-2-methylpyridine and [(1S)-Endo]-(−)-borneol. Yield: 69%; M.p.: 98° C.

$^1$H-NMR (100 MHz, CDCl$_3$)=8.1 (d, 1H), 7.5 (d, 1H), 4.4 (m, 1H), 3.9 (s, 3H), 2.5 (s, 3H), 0.9 to 2.6 (m, 7H), 0.9 (2s, 9H) ppm

Example 47 cis-Bicyclo[4.4.0]dec-3-yl 3-methoxy-2-methylpyrid-4-yl ether hydrochloride

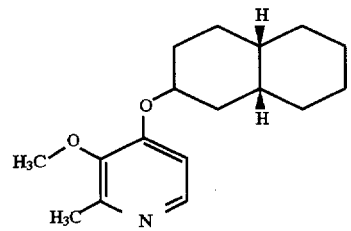

Preparation was carried out analogously to Example 43 from 4-chloro-3-methoxy-2-methylpyridine and cis-bicyclo[4.4.0]decan-3-ol. Yield: 32%; m.p.: 142° C.

¹H-NMR (100 MHz, D₂O)=8.2 (d, 1H), 7.4 (d, 1H), 4.8 (m, 1H), 3.9 (s, 3H), 2.6 (s, 3H), 1.2 to 2.0 (m, 16H) ppm

Example 48

4-(4-Oxocyclohexyloxy)-3-methoxy-2-methylpyridine 1 g of 4-(3,3-dimethyl-1,5-dioxaspiro[5.5]undecan-9-yloxy)-3-methoxy-2-methylpyridine is stirred with 20 ml of formic acid and 5 ml of acetone for 5 hours. The residue which remains after concentrating is purified by chromatography on silica gel using ethyl acetate. 0.3 g=41%; m.p.: 56° to 57° C.

¹H-NMR (100 MHz, CDCl₃)=8.1 (d, 1H), 6.8 (d, 1H), 4.8 (m, 1H), 3.8 (s, 3H), 2.5 (s, 3H), 1.9 to 2.8 (m, 8H) ppm

Example 49

3,5-Dichloro-4-[4-cis-(1,1,3,3-tetramethylbut-1-yl)cyclohexyloxy]pyridine

A mixture of 1.82 g (10 mmol) of 3,4,5-trichloropyridine, 2.76 g (13 mmol) of 4-cis-(1,1,3,3-tetramethylbut-1-yl)cyclohexanol and 15 ml of DMSO is added dropwise at 25° C. to 0.36 g (12 mmol) of NaH (80% strength) in 25 ml of DMSO. The mixture is then stirred at 60° C. for 6 hours. For working up, saturated ammonium chloride solution is added at 20° to 25° C. and the mixture is extracted with ethyl acetate. The reaction product is purified by chromatography (SiO₂; diisopropyl ether). Yield: 2.85 g (79.5%)

¹H-NMR (CDCl₃)=8.4 (s, 2H), 4.9 (m, 1H), 1.0 to 2.2 (m, 9H), 1.3 (s, 2H), 0.9 and 0.95 (2s, 15H) ppm

Example 50

2-Methyl-3-chloro-4-(4-cis-phenylcyclohexyloxy)pyridine

A mixture of 1.62 g (10 mmol) of 1-methyl-3,4-dichloropyridine, 2.29 g (13 mmol) of 4-cis-phenylcyclohexanol and 30 ml of DMSO is added dropwise to 0.36 g (12 mmol) of NaH (80% strength) in 25 ml of DMSO. The mixture is then stirred at 40° C. for 1.5 hours and at 60° C. for 5 hours. For working up, saturated ammonium chloride solution is added at 20° to 25° C. and the mixture is extracted with ethyl acetate. The reaction product is purified by chromatography (SiO₂; diisopropyl ether/EtOAc [1:1]). Yield: 1.6 g (53%); m.p.: 79° C.

¹H-NMR (CDCl₃)=8.2 (d, 1H), 7.1 to 7.4 (m, 5H), 6.8 (d, 1H), 4.4 (m, 1H), 2.6 (s, 3H), 1.0 to 2.0 (m, 9H) ppm

Example 51

2-Methyl-3-methoxy-4-[2-(4-tert-butylphenoxy)ethoxy]pyridine

A mixture of 1.57 g (10 mmol) of 2-methyl-3-methoxy-4-chloropyridine, 2.52 g (13 mmol) of 2-(4-tert-butylphenoxy)ethanol and 15 ml of DMSO is added dropwise at 25° C. to 0.36 g (12 mmol) of NaH (80% strength) in 25 ml of DMSO. The mixture is then stirred at 60° C. for 5 hours. For working up, saturated ammonium chloride solution is added at 20° to 25° C. and the mixture is extracted with ethyl acetate. The reaction product is purified by chromatography (SiO₂; EtOAc). Yield: 2.63 g (74.9%); m.p.: 84° to 87° C.

¹H-NMR (CDCl₃)=8.1 (d, 1H), 6.8 to 7.3 (m, 4H), 6.7 (d, 1H), 4.4 (s, 4H), 3.8 (s, 3H), 2.5 (s, 3H), 1.3 (s, 9H) ppm

Example 52

4-(O-Benzylhydroxylamino)-3-chloro-2-ethylpyridine

Preparation was carried out analogously to Example 1 from 3,4-dichloro-2-ethylpyridine and O-benzylhydroxylamine. Yield: 99%

¹H-NMR (100 MHz, CDCl₃): δ: 8.2 (d, 1H), 7.6 (s, 1H), 7.4 (m, 5H), 6.9 (d, 2H), 4.9 (s, 2H), 2.9 (q, 2H), 1.3 (t, 3H) ppm.

Example 53

4[O-Benzyl-N-(4-cis-[1,1,3,3-tetramethylbut-1-yl]cyclohexyl)hydroxylamino]-3-chloro-2-ethylpyridine Preparation was carried out analogously to Example 7 from 4-(O-benzylhydroxylamino)-3-chloro-2-ethylpyridine (Example 52) and trans-1-(4-toluenesulfonyloxy)-4-(1,1,3,3-tetramethylbutyl)cyclohexane. Yield: 41%

¹H-NMR (100 MHz, CDCl₃): δ: 8.4 (d, 1H), 7.3 (m, 6H), 4.6 (s, 2H), 3.5 (m, 1H), 3.0 (q, 2H), 1.3 (t, 3H), 0.9 (s, 6H), 1.0 (s, 9H), 0.8–2.0 (m, 10H) ppm.

Example 54

4-[O-Benzyl-N-(4-cis-phenylcyclohexyl)hydroxylamino]-3-chloro-2-ethylpyridine

Preparation took place analogously to Example 7 from 4-(O-benzylhydroxylamino)-3-chloro-2-ethylpyridine (Example 52) and trans-1-(4-toluenesulfonyloxy)-4-phenylcyclohexane Yield: 64%

¹H-NMR (100 MHz, CDCl₃): δ: 8.3 (d, 1H), 7.2 (m, 11H), 4.6 (s, 2H), 3.6 (m, 1H), 3.0 (q, 2H), 2.8 (m, 1H), 1.3 (t, 3H), 1.2–2.2 (m, 8H) ppm.

Example 55

4-[4-cis(1,1,3,3-Tetramethylbutyl)cyclohexylamino]-3-chloro-2-ethylpyridine 5.6 g of 4-[O-benzyl-N-(4-cis-[1,1,3,3-tetramethylbut-1-yl]cyclohexyl)hydroxylamino]-3-chloro-2-ethylpyridine in 20 ml of methanol and 5 ml of glacial acetic acid are stirred with 4 g of zinc dust for 4 hours. The solution is filtered and concentrated. The residue is shaken with sodium hydroxide solution and methylene chloride. The methylene chloride phase is chromatographed on silica gel after concentrating. Eluent: ethyl acetate/hexane 1:4. Yield: 4 g=90%

¹H-NMR (100 MHz, CDCl₃): δ: 8.1 (d, 1H), 6.4 (d, 1H), 5.1 (d, 1H), 3.7 (m, 1H), 2.9 (q, 2H), 1.3 (t, 3H), 1.0 (s, 6H), 1.0 (s, 9H), 1.2–2.0 (m, 10H) ppm.

Example 56

4-(4-cis-Phenylcyclohexylamino)-3-chloro-2-ethylpyridine

Was prepared analogously to Example 55 from 4-[O-benzyl-N-(4-cis-phenylcyclohexyl)hydroxylamino]-3-chloro-2-ethylpyridine (Example 54). Yield: 70%

¹H-NMR (100 MHz, CDCl₃): δ: 8.1 (d, 2H), 7.3 (m, 5H), 6.4 (d, 2H), 5.1 (d, 2H), 3.8 (m, 1H), 2.9 (q, 2H), 2.6 (m, 1H), 2.9 (q, 2H), 2.6 (m, 1H), 1.3 (t, 3H), 1.6–2.0 (m, 8H) ppm.

Example 57

4-[O-Benzyl-N-(spiro[5.5]undecan-3-yl)hydroxylamino]-3-chloro-2-ethylpyridine

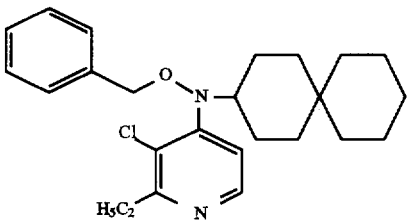

Was prepared analogously to Example 7 from 4-(O-benzylhydroxylamino)-3-chloro-2-ethylpyridine (Example 52) and 3-tosyloxyspiro[5.5]undecane. Yield: 95%

$^1$H-NMR (100 MHz, CDCl$_3$): δ: 8.3 (d, 1H), 7.3 (m, 5H), 7.2 (d, 1H), 4.8 (s, 2H), 3.4 (m, 1H), 3.0 (q, 2H), 1.3 (t, 3H), 0.9–1.9 (m, 18H) ppm.

Example 58

4-(Spiro[5.5]undecan-3-yl)amino-3-chloro-2-ethylpyridine

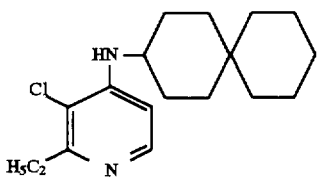

Was prepared analogously to Example 55 from 4-[O-benzyl-N-(spiro[5.5]undecan-3-yl)hydroxylamino]-3-chloro-2-ethylpyridine (Example 57). Yield: 51%

$^1$H-NMR (100 MHz, CDCl$_3$): δ: 8.1 (d, 1H), 6.4 (d, 1H), 4.8 (d, 1H), 3.3 (m, 1H), 2.8 (q, 2H), 1.3 (t, 3H), 1.2–2.0 (m, 18H) ppm.

Example 59

3-Chloro-4-[4-(2,4-dichlorobenzylidene)cyclohexyl]amino-2-ethylpyridine 1.6 g of 3,4-dichloro-2-ethylpyridine and 2.5 g of 4-(2,4-dichlorobenzylidene)cyclohexylamine are heated at 180° C. for 3.5 hours together with 55 g of ammonium chloride in 9 ml of N-methylpyrrolidone. After cooling, the mixture is poured into saturated sodium bicarbonate solution and extracted with ethyl acetate. The product is purified by chromatography on silica gel using ethyl acetate/heptane 1:4. Yield: 7%

$^1$H-NMR [100 MHz, CDCl$_3$]: δ: 8.1 (d, 2H), 7.1–7.4 (m, 3H), 6.4 (d, 1H), 6.3 (d, 1H), 4.8 (d, 1H), 3.6 (m, 1H), 2.9 (q, 2H), 1.6–2.6 (m, 8H), 1.3 (t, 3H) ppm

Example 60

3-Chloro-4-(4-cis-cyclohexylcyclohexyl)amino-2-ethylpyridine

Was prepared analogously to Example 59 from 3,4-dichloro-2-ethylpyridine and 4-cyclohexylcyclohexylamine and subsequent isomer separation on Sephadex using methanol. Yield: 10% (cis-isomer)

$^1$H-NMR (100 MHz, CDCl$_3$): δ: 8.1 (d, 1H), 6.4 (d, 1H), 5.0 (d, 1H), 3.7 (m, 1H), 2.8 (q, 1H), 1.3 (t, 3H), 0.8–1.9 (m, 20H) ppm.

Example 61

3-Chloro-4-(4-trans-cyclohexylcyclohexyl)amino-2-ethylpyridine

For preparation see Example 60 Yield: 4% (trans-isomer)

$^1$H-NMR (100 MHz, CDCl$_3$): δ: 8.1 (d, 1H), 6.4 (d, 1H), 4.6 (d, 1H), 3.2 (m, 1H), 2.8 (q, 1H), 1.2 (t, 3H), 0.8–2.2 (m, 20H) ppm.

Example 62

3-Chloro-4-[4-(4-(2-methoxyethoxy)phenyl)cyclohexylamino)-2-ethylpyridine

Preparation took place analogously to Example 59 from 3,4-dichloro-2-ethylpyridine and 4-(4-(2-methoxyethoxy)phenyl)cyclohexylamine. Yield: 11% (cis/trans mixture)

$^1$H-NMR (100 MHz, CDCl$_3$): δ: 8.1 (2d, 1H), 7.0 (m, 4H), 6.4 (2d, 1H), 5.1 and 4.7 (2d, 1H), 3.4 and 3.8 (2m, 1H), 3.7 (m, 2H), 4.1 (m, 2H), 3.5 (2s, 3H), 2.9 (2q, 2H), 1.4–2.6 (m, 9H), 1.3 (2t, 3H) ppm.

Example 63

3-Chloro-4-[4-cis-(4-ethoxyphenyl)cyclohexylamino]-2-ethylpyridine

Preparation took place analogously to Example 59 from 3,4-dichloro-2-ethylpyridine and 4-(4-ethoxyphenyl)cyclohexylamine and isomer separation on ®Sephadex using methanol. Yield: 11%

$^1$H-NMR (100 MHz, CDCl$_3$): δ: 8.1 (d, 1H), 7.0 (m, 4H), 6.4 (d, 1H), 5.1 (d, 1H), 4.0 (q, 2H), 3.8 (m, 1H), 2.9 (q, 2H), 2.6 (m, 1H), 1.6–2.1 (m, 8H), 1.3 (t, 3H), 1.4 (t, 3H) ppm.

Example 64

3-Chloro-4-[4-cis-(4-(2-ethoxyethyloxy)phenyl)]cyclohexylamino-2-ethylpyridine

Preparation was carried out analogously to Example 60 from 3,4-dichloro-2-ethylpyridine and 4-cis-(4-(2-ethoxyethyloxy)phenyl)cyclohexylamine. Yield: 10%

$^1$H-NMR (100 MHz, CDCl$_3$): δ: 8.1 (d, 1H), 7.0 (m, 4H), 6.4 (d, 1H), 5.1 (d, 1H), 4.1 (q, 2H), 3.8 (q, 2H), 3.8 (m, 1H), 3.6 (q, 2H), 2.9 (q, 2H), 1.4–2.6 (m, 9H), 1.2 (t, 3H) ppm.

Example 65

3-Chloro-4-[4-cis(1,1,3,3-tetramethylbutyl)cyclohexylamino]-2-methylpyridine

Preparation was carried out analogously to Example 59 from 3,4-dichloro-2-methylpyridine and 4-(1,1,3,3-tetramethylbutyl)cyclohexylamine. Isomer separation was carried out by chromatography on silica gel using ethyl acetate/hexane 1:1 and Sephadex/methanol. Yield: 33% (cis-isomer)

$^1$H-NMR (100 MHz, CDCl$_3$): δ: 8.0 (d, 1H), 6.4 (d, 1H), 5.0 (d, 1H), 3.7 (m, 1H), 2.5 (s, 3H), 1.2–2.2 (m, 11H), 1.0 (s, 9H), 0.9 (s, 6H) ppm.

Example 66

3-Chloro-4-[4-trans-(1,1,3,3-tetramethylbutyl)cyclohexylamine]-2-methylpyridine trans-isomer to Example 65 Yield: 14% (trans-isomer)

¹H-NMR (100 MHz, CDCl₃): δ: 8.0 (d, 1H), 6.4 (d, 1H), 4.6 (d, 1H), 3.2 (m, 1H), 2.5 (s, 3H), 1.2–2.2 (m, 11H), 1.0 (s, 9H), 0.9 (s, 6H) ppm.

Example 67

3-Chloro-4-[N-(4-fluorophenyl)piperidinyl]amino-2-methylpyridine

Preparation was carried out analogously to Example 59 from 3,4-dichloro-2-methylpyridine and 4-amino-N-(4-fluorophenyl)piperidine. Yield: 22%

¹H-NMR (100 MHz, CDCl₃): δ: 8.1 (d, 2H), 6.9 (m, 2H), 6.4 (d, 1H), 4.8 (d, 1H), 2.5 (s, 3H), 1.6–3.7 (m, 9H) ppm.

Example 68

3-Chloro-4-[4-cis-cyclohexyloxy]cyclohexylamino-2-methylpyridine

Preparation took place analogously to Example 59 from 3,4-dichloro-2-methylpyridine and 4-cis-cyclohexyloxy-cyclohexylamine. Yield: 15%

¹H-NMR (100MHz, CDCl₃): δ: 8.0 (d, 1H), 6.4 (d, 1H), 4.8 (d, 1H), 3.1–3.7 (m, 3H), 2.5 (s, 3H), 1.1–1.9 (m, 18H) ppm.

Example 69

3-Chloro-4-(3-isoamylcyclopentyl)amino-2-methylpyridine

Preparation was carried out as in Example 59 from 3,4-dichloro-2-methylpyridine and 3-isoamylcyclopentylamine. Yield: 61%

¹H-NMR (100 MHz, CD₃OD): δ: 7.9 (d, 1H), 6.4 (d, 1H), 3.9 (m, 1H), 2.4 (s, 3H), 1.2–2.3 (m, 9H), 0.9 (t, 3H), 0.9 (s, 6H) ppm.

Example 70

3-Chloro-4-[4-cis-(cyclohexyl-1-methylethyl)cyclohexyloxy]-2-methylpyridine

The solution formed from 1.6 g of 3,4-dichloro-2-methylpyridine and 2.5 g of 4-cis-(1-cyclohexyl-1-methylethyl)cyclohexanol is added dropwise with stirring to 330 mg of NaH in 30 ml of DMSO and the mixture is heated at 40° C. for 2 hours. After cooling pH 7 is set using aqueous ammonium chloride solution and the product is extracted with ethyl acetate. Purification is carried out by chromatography on silica gel using ethyl acetate/heptane 7:3 and on ®Sephadex using methanol. Yield: 60%

¹H-NMR (100 MHz, CDCl₃): δ: 8.2 (d, 1H), 6.7 (d, 1H), 4.7 (m, 1H), 2.6 (s, 3H), 0.8–2.2 (m, 20H), 0.7 (s, 6H) ppm.

Example 71

3-Chloro-4-[4-(4-fluorobenzylidene)cyclohexylamino]-2-methylpyridine

Synthesis was carried out analogously to Example 59 from 3,4-dichloro-2-methylpyridine and 4-(4-fluorobenzylidine)cyclohexylamine. Yield: 25%

¹H-NMR (100 MHz, CDCl₃): δ: 8.0 (d, 1H), 7.1 (m, 4H), 6.4 (d, 1H), 6.3 (s, 1H), 4.8 (d, 1H), 3.6 (m, 1H), 2.5 (s, 3H), 1.3–2.9 (m, 8H) ppm.

Example 72

3-Chloro-4-[4-(4-(2-ethoxyethoxy)ethoxy)phenyl]cyclohexylamino-2-methylpyridine

Preparation took place analogously to Example 59 from 3,4-dichloro-2-methylpyridine and 4-[4-(2-ethoxyethoxy)ethyloxy)phenyl]cyclohexylamine. Yield: 37% (cis/trans mixture)

¹H-NMR (100 MHz, CD₃OD): δ: 7.9 (d, 1H), 7.0 (m, 4H), 6.4 (d, 1H), 3.4–4.1 (m, 10H), 2.6 (m, 1H), 2.5 (s, 3H), 1.4–2.1 (m, 9H), 1.2 (t, 3H) ppm.

Example 73

3-Bromo-4-[4-(4-(2-ethoxyethoxy)ethyloxy)phenyl]cyclohexylamino-2-methylpyridine The compound was prepared analogously to Example 59 from 3-bromo-4-chloro-2-methylpyridine and 4-[4-(2-ethoxyethoxy)ethyloxy)phenyl]cyclohexylamine. Yield: 11%

¹H-NMR (100 MHz, CDCl₃): δ: 8.1 (d, 1H), 7.0 (m, 4H), 6.4 (d, 1H), 5.2 (d, 1H), 3.4–4.2 (m, 10H), 2.6 (s, 3H), 2.5 (m, 1H), 1.2–2.1 (m, 9H), 1.2 (t, 3H) ppm.

Example 74

3-Bromo-4-[4-(4-fluorobenzylidene)]cyclohexylamino-2-methylpyridine

Preparation was carried out analogously to Example 59 from 3-bromo-4-chloro-2-methylpyridine and 4-(4-fluorobenzylidene)cyclohexylamine. Yield: 48%

¹H-NMR (100 MHz, CDCl₃): δ: 8.0 (d, 1H), 7.1 (m, 4H), 6.4 (d, 1H), 6.3 (s, 1H), 3.8 (d, 1H), 3.6 (m, 1H), 2.6 (s, 3H), 1.2–2.9 (m, 8H) ppm.

Example 75

2-Ethyl-3-bromo-4-(cis-4-phenylcyclohexylamino)pyridine 3.48 g (20 mmol) of 4-phenylcyclohexanone in 3.3 ml of ethanol are treated with 3.3 ml of triethyl orthoformate and 2 drops of boron trifluoride etherate and warmed at 50° C. for 30 min. After addition of 2.01 g (10mmol) of 2-ethyl-3-bromo-4-aminopyridine the reaction mixture is heated at 135°–140° C. for 3.5–4 hours with simultaneous removal of the low-boiling components by distillation. It is then cooled, 40 ml of dichloroethane, 3.18 g (15 mmol) of sodium triacetoxyborohydride and 0.57 ml (10 mmol) of glacial acetic acid are added, and it is heated at 50°–60° C. for 3 hours; the reaction mixture is then cooled, saturated aqueous sodium hydrogen carbonate solution is added, the 1,2-dichloroethane is evaporated and the reaction product is extracted from the aqueous phase using ethyl acetate. Purification is carried out by column chromatography. Yield: 1.46 g (41%); $R_F$=0.59 (ethyl acetate)

¹H-NMR (CDCl₃): δ: 8.10 (d, 1H), 7.18–7.36 (m, 5H), 6.36 (d, 1H), 5.24 (d, 1H), 3.80 (m, 1H), 2.92 (q, 2H), 2.63 (m, 1H), 1.64–2.08 (m, 8H), 1.29 (t, 3H) ppm.

Example 76

2-Ethyl-3-bromo-4-(trans-4-phenylcyclohexylamino)pyridine

As Example 75 Yield: 0.5 g (14 %); $R_F$=0.72 (ethyl acetate)

¹H-NMR (CDCl₃): δ: 8.12 (d, 1H), 7.20–7.35 (m, 5H), 6.36 (d, 1H), 4.84 (d, 1H), 3.40 (m, 1H), 2.90 (q, 2H), 2.50 (m, 1H), 1.30–2.3 (m, 8H), 1.30 (t, 3H) ppm.

Example 77

2-Ethyl-3-bromo-4-[cis-4-(4-ethoxyphenyl)cyclohexylamino]pyridine

As Example 75 or 4.36 g (20 mmol) of 4-(4-ethoxyphenyl)cyclohexanone instead of 4-phenylcyclohexanone. Yield: 1.7 g (42%); $R_F$=0.51 (ethyl acetate)

¹H-NMR (CDCl₃): δ: 8.10 (d, 1H), 6.82–7.18 (AA'BB', 4H), 6.36 (d, 1H), 5.22 (d, 1H), 4.01 (q, 2H), 3.81 (m, 1H), 2.92 (q, 2H), 2.58 (m, 1H), 1.6–2.05 (m, 8H), 1.4 (t, 3H), 1.28 (t, 3H) ppm.

Example 78

2-Ethyl-3-bromo-4-[trans-4-(3-ethoxyphenyl)cyclohexylamino]pyridine

As Example 77 Yield: 590 mg; R_f=0.63 (ethyl acetate)

¹H-NMR (CDCl₃): δ: 8.10 (d, 1H), 6.80–7.16 (AA'BB'4H), 6.38 (d, 1H), 4.80 (d, 1H), 4.01 (q, 2H), 3.38 (m, 1H), 2.90 (q, 2H), 2.53 (m, 1H), 1.30–2.30 (m, 8H), 1.40 (t, 3H), 1.27 (t, 3H) ppm.

Example 79

2-Ethyl-3-bromo-4-[cis-4-(1,1,3,3-tetramethylbutyl)cyclohexylamino]pyridine

As Example 75, but using 4.2 g (20 mmol) of 4-(1,1,3,3-tetramethylbutyl)cyclohexanone instead of 4-phenylcyclohexanone. Yield: 1.86 g (47%); R_f=0.63 (ethyl acetate)

¹H-NMR (CDCl₃): δ: 8.09 (d, 1H), 6.32 (d, 1H), 5.15 (d, 1H), 3.74 (m, 1H), 2.90 (q, 2H), 1.20 to 2.10 (m, 14H), 0.99 (s, 9H), 0.96 (s, 6H) ppm.

Example 80

2-Ethyl-4-[cis-4-(1,1,3,3-tetramethylbutyl)cyclohexylamino]-5-bromopyridine

As Example 75, but using 2.01 g (10 mmol) of 4-ethyl-4-amino-5-bromopyridine instead of 2-ethyl-3-bromo-4-aminopyridine and 4.2 g (20 mmol) of 4-(1,1,3,3-tetramethylbutyl)cyclohexanone instead of 4-phenylcyclohexanone. Yield: 1.9 g (48%); R_f=0.39 (diisopropyl ether)

¹H-NMR (CDCl₃): δ: 8.26 (d, 1H), 6.34 (s, 1H), 4.96 (d, 1H), 3.77 (m, 1H), 2.66 (q, 2H), 1.20 to 2.15 (m, 1H), 0.99 (s, 9H), 0.96 (s, 6H) ppm.

Example 81

2-Chloro-3-methoxy-4-[cis-4-(1,1,3,3-tetramethylbutyl)cyclohexylamino]pyridine

As Example 75, but using 1.58 g (10 mmol) of 4-chloro-3-methoxy-4-aminopyridine instead of 2-ethyl-3-bromo-4-aminopyridine and 4.2 g (20 mmol) of 4-(1,1,3,3-tetramethylbutyl)[cyclohexanone instead of 4-phenylcyclohexanone. Yield: 1.5 g (42.5%); R_f=0.62 (diisopropyl ether)

¹H-NMR (CDCl₃): δ: 7.81 (d, 1H), 6.44 (d, 1H), 5.00 (d, 1H), 3.85 (s, 3H), 3.67 (m, 1H), 1.1 to 2.02 (m, 11H), 0.99 (s, 9H), 0.96 (s, 6H) ppm.

Example 82

2-Chloro-3-methoxy-4-[trans-4-(1,1,3,3-tetramethylbutyl)cyclohexylamino]pyridine As Example 81. Yield: 0.4 g (14%); R_f=0.73 (diisopropyl ether)

¹H-NMR (CDCl₃): δ: 7.80 (d, 1H), 6.46 (d, 1H), 4.66 (d, 1H), 3.80 (s, 3H), 3.18 (m, 1H), 1.10 to 2.10 (m, 1H), 0.99 (s, 9H), 0.96 (s, 6H) ppm.

Example 83

2,3-Dimethoxy-4-[cis-4-(1,1,3,3-tetramethylbutyl)cyclohexylamino]pyridine

As Example 75, but using 1.54 g (10 mmol) of 2,3-dimethoxy-4-aminopyridine instead of 2-ethyl-3-bromo-4-amino-pyridine and 4.2 g (20 mmol) of 4-(1,1,3,3-tetramethylbutyl)cyclohexanone instead of 4-phenylcyclohexanone.

Purification is carried out by crystallization of the hydrochloride. Yield: 1.5 g (43%)

¹H-NMR (CDCl₃): δ: 7.65 (d, 1H), 6.25 (d, 1H), 4.86 (d, 1H), 3.96 (s, 3H), 3.80 (s, 3H), 1.10 to 2.02 (m, 11H), 0.99 (s, 9H), 0.95 (s, 6H) ppm.

Example 84

2,3-Dimethoxy-4-(cis-4-phenylcyclohexylamino)pyridine

As Example 83, but using 3.48 g (20 mmol) of 4-phenylcyclohexanone instead of 4-(1,1,3,3-tetramethylbutyl)cyclohexanone. Yield: 1.25 g (40%); R_f=0.49 (diisopropyl ether)

¹H-NMR (CDCl₃): δ: 7.67 (d, 1H), 7.15 to 7.35 (m, 5H), 6.28 (d, 1H), 4.94 (d, 1H), 3.97 (s, 3H), 3.84 (s, 3H), 3.75 (m, 1H), 1.25 to 2.6 (m, 9H) ppm.

Example 85

2,3-Dimethoxy-4-(trans-4-phenylcyclohexylamino)pyridine

As Example 84. Yield: 0.66 g (21%); m.p. 137° C.

¹H-NMR (CDCl₃): δ: 7.66 (d, 1H), 7.15 to 7.35 (m, 5H), 6.30 (d, 1H), 4.56 (d, 1H), 3.96 (s, 3H), 3.78 (s, 3H), 3.34 (m, 1H), 1.25 to 2.6 (m, 9H) ppm.

Example 86

2,3-Dimethoxy-4-(cis-4-(4-ethoxyphenyl)cyclohexylamino)]pyridine

As Example 83, but using 4.36 g (20 mmol) of 4-(4-ethoxyphenyl)cyclohexanone instead of 4-(1,1,3,3-tetramethylbutyl)cyclohexanone. Yield: 1.43 g (40%); m.p. 99° C.

¹H-NMR (CDCl₃): δ: 7.66 (d, 1H), 6.80 to 7.17 (m, 4H), 6.28 (d, 1H), 4.94 (d, 1H), 4.02 (q, 2H), 3.97 (s, 3H), 3.83 (s, 3H), 3.73 (m, 1H), 2.58 (m, 1H), 1.60 to 2.05 (m, 8H), 1.40 (3, 3H) ppm.

Example 87

3-Chloro-2-isopropyl-4-(cis-4-phenylcyclohexylamino)pyridine

Was prepared analogously to Example 75 starting from 4-amino-3-chloro-2-isopropylpyridine and 4-phenylcyclohexanone. Yield: 26.6%

¹H-NMR (CDCl₃): δ: 8.2 (d, 1H), 7.2 to 7.4 (m, 5H), 6.4 (d, 1H), 5.2 (d, 1H), 3.8 (m, 1H), 3.5 (m, 1H), 2.6 (m, 1H), 1.6 to 2.1 (m, 8H), 1.3 (d, 6H) ppm.

Example 88

3-Chloro-2-isopropyl-4-[4-cis-(4-ethoxyphenyl)cyclohexylamino]pyridine

Was prepared analogously to Example 75 starting from 4-amino-3-chloro-2-isopropylpyridine and 4-phenylcyclohexanone. Yield: 19.4%

¹H-NMR (CDCl₃): δ: 8.2 (d, 1H), 6.8 to 7.2 (m, 4H), 6.4 (d, 1H), 5.1 (d, 1H), 4.0 (q, 2H), 3.8 (m, 1H), 3.5 (m, 1H), 2.6 (m, 1H), 1.6 to 2.1 (m, 8H), 1.4 (t, 3H), 1.3 (d, 6H) ppm.

Example 89

3-Chloro-2-isopropyl-4-[4-cis-(1,1,3,3-tetramethylbutyl)-cyclohexylamino]pyridine Was prepared analogously to Example 75 starting from 4-amino-3-chloro-2-isopropylpyridine and 4-(1,1,3,3-tetramethylbutyl)cyclohexanone. Yield: 39.8%

¹H-NMR (CDCl₃): δ: 8.2 (d, 1H), 6.4 (d, 1H), 5.1 (d, 1H), 3.7 (m, 1H), 3.5 (m, 1H), 1.0 to 2.0 (m, 32H) ppm.

Example 90

2-Ethyl-3-methoxy-4-O-benzylhydroxylaminopyridine

Was prepared analogously to Example 1 from 2-ethyl-3-methoxy-4-chloropyridine and O-benzylhydroxylamine. Yield: 68%

¹H-NMR (CDCl₃): δ: 8.1 (d, 1H), 7.2 to 7.6 (m, 5H), 6.9 (d, 1H), 4.9 (s, 2H), 3.6 (s, 3H), 2.8 (q, 2H), 1.3 (t, 3H) ppm.

Example 91

4-[O-Benzyl-N-(4-cis-phenylcyclohexyl)hydroxylamino]-3-methoxy-2-ethylpyridine

Was prepared analogously to Example 7 from 2-ethyl-3-methoxy-4-O-benzylhydroxylaminopyridine and trans-1-(4-toluenesulfonyloxy)-4-phenylcyclohexanone. Yield: 62.4%

¹H-NMR (CDCl₃): δ: 8.2 (d, 1H), 7.1 to 7.3 (m, 11H), 4.7 (s, 2H), 3.8 (s, 3H), 3.7 to 3.8 (m, 1H), 2.8 (q, 2H), 1.5 to 2.3 (m, 9H), 1.3 (t, 3H) ppm.

Example 92

2-Ethyl-3-methoxy-4-(4-cis-phenylcyclohexyl)aminopyridine

Was prepared analogously to Example 15 from 4-[O-benzyl-N-(4-cis-phenylcyclohexyl)hydroxylamino]-3-methoxy-2-ethylpyridine.

¹H-NMR (CDCl₃): δ: 8.0 (d, 1H), 7.2 to 7.4 (m, 5H), 6.4 (d, 1H), 4.9 (d, 1H), 3.8 (s, 3H), 3.7 (m, 1H), 2.8 (2, 2H), 2.6 (m, 1H), 1.6 to 2.1 (m, 8H), 1.3 (t, 3H) ppm.

Example 93

2-Ethyl-3-methoxy-4-[O-benzyl-N-(4-cis-[4-ethoxyphenyl]cyclohexyl)hydroxylamino]pyridine Was prepared analogously to Example 13 using 2-ethyl-3-methoxy-4-(O-benzylhydroxylamino)pyridine instead of 2-methyl-3-methoxy-4-(O-benzylhydroxylamino) pyridine. Yield: 63.0%

¹H-NMR (CDCl₃): δ: 8.1 (d, 2H), 7.1 to 7.4 (m, 9H), 6.8 (d, 1H), 4.7 (d, 2H), 4.0 (q, 2H), 3.8 (s, 3H), 3.7 (m, 1H), 2.8 (q, 2H), 1.5 to 2.3 (m, 9H), 1.4 (t, 3H) ppm.

Example 94

2-Ethyl-3-methoxy-4-[4-cis-(4-ethoxyphenyl)cyclohexylamino]pyridine

Was prepared analogously to Example 17 from 2-ethyl-3-methoxy-4-[O-benzyl-N-(4-cis-[4-ethoxyphenyl]cyclohexyl)hydroxylamino]pyridine. Yield: 71.6%

¹H-NMR (CDCl₃): δ: 8.0 (d, 1H), 6.8 to 7.1 (m, 4H), 6.4 (d, 1H), 4.9 (d, 1H), 4.0 (q, 2H), 3.8 (s, 3H), 3.7 (m, 1H), 2.7 (q, 2H), 2.6 (m, 1H), 1.6 to 2.0 (m, 8H), 1.4 (t, 3H), 1.3 (t, 3H) ppm.

Example 95

3-Chloro-2-ethyl-4-(4-cis-trimethylsilylcyclohexylamino)-pyridine

A solution of 200 mg (4.5 mmol) of 3,4-dichloro-2-ethylpyridine, 1.70 g (9.9 mmol) of cis-4-trimethylsilylcyclohexylamine (cis, trans mixture) and 150 mg of ammonium chloride in 5 ml of N-methylpyrrolidone is stirred at 180° C. for 18 hours. After cooling to room temperature, 10 ml of sodium hydrogencarbonate solution are added and the mixture is extracted thoroughly with ether. The combined organic phase is then washed with satd. sodiumchloride solution, and the organic phase is dried using magnesium sulfate and concentrated in vacuo. The residue is purified by flash chromatography (SiO₂, ethyl acetate). 0.4 g of the clean cis isomer and 0.2 g of the trans compound are obtained (42.5%). The title compound is a brown resin.

¹H-NMR (80 MHz): 8.05 (d, 1H), 6.32 (m, 1H), 5.02 (m, 1H), 3.75 (m, 1H), 2.85 (q, 2H), 2.0 to 0.4 (m, 12H) ppm.

Example 96

2-Chloro-3-bromo-4-(cis-4-phenylcyclohexylamino)-pyridine 2.27 g (10 mmol) of 2,4-dichloro-3-bromopyridine, 2.6 g (15 mmol) of cis-4-phenylcyclohexylamine and 0.1 g of ammonium chloride are heated at 120° C. for 10 hours in 10 ml of N-methylpyrrolidone. After cooling, saturated sodium hydrogencarbonate solution is added and the reaction product is extracted with ethyl acetate. Purification is carried out by column chromatography. Yield: 1.9 g (52%); m.p. 105° C.

¹H-NMR (CDCl₃): δ: 7.96 (d, 1H), 7.18 to 7.36 (m, 5H), 6.42 (d, 1H), 5.36 (d, 1H), 3.85 (m, 1H), 2.65 (m, 1H), 1.5 to 2.2 (m, 8H) ppm.

Example 97

2-Chloro-3-bromo-4-(trans-phenylcyclohexylamino)pyridine

As Example 96 using trans-4-phenylcyclohexylamine. Yield: 1.8 g (49%); m.p. 85° C.

¹H-NMR (CDCl₃): δ: 7.95 (d, 1H), 7.18 to 7.36 (m, 5H), 6.45 (d, 1H), 4.95 (d, 1H), 3.40 (m, 1H), 2.58 (m, 1H), 1.35 to 1.75 (m, 8H) ppm.

Example 98

2-Methoxy-3-bromo-4-(cis-4-phenylcyclohexylamino)pyridine 2.21 g (6.04 mmol) of 2-chloro-3-bromo-4-(cis-4-phenylcyclohexylamino)pyridine in 30 ml of dimethylformamide are treated with 4.31 ml of 30% strength solution of sodium methoxide in methanol and the mixture is heated at 80° C. for 1 hour. After cooling, water is added, the mixture is adjusted to pH 8 using ½ conc. hydrochloric acid and the reaction product is extracted with ethyl acetate. For purification it is chromatographed. Yield: 1.72 g (79%); R_f=0.4 (diisopropyl ether)

¹H-NMR (CDCl₃): δ: 7.80 (d, 1H), 7.18 to 7.36 (m, 5H), 6.26 (d, 1H), 5.18 (d, 1H), 3.85 (m, 1H), 3.95 (s, 3H), 2.63 (m, 1H), 1.6 to 2.1 (m, 8H) ppm.

Example 99

2-Methoxy-3-bromo-4-(trans-4-phenylcyclohexylamino)pyridine

As Example 98, from 2-chloro-3-bromo-4-(trans-4-phenylcyclohexylamino)pyridine. Yield: 64%; m.p. 105° C.

¹H-NMR (CDCl₃): δ: 7.79 (d, 1H), 7.16 to 7.36 (m, 5H), 6.28 (d, 1H), 4.74 (d, 1H), 3.97 (s, 1H), 3.40 (m, 1H), 2.56 (m, 1H), 1.3 to 2.32 (m, 8H) ppm.

B. Formulation Examples a) A dusting composition is obtained by mixing 10% by weight of active compound and 90 parts by weight of talc as inert substance and comminuting in a hammer mill.

b) A wettable powder which is easily dispersible in water is obtained by mixing 25 parts by weight of active compound, 65 parts by weight of kaolin-containing quartz as inert substance, 10 parts by weight of potassium lignosulfonate and one part by weight of sodium oleoylmethyltaurate as wetting agent and dispersant and grinding in a pinned disc mill.

c) A dispersion concentrate which is easily dispersible in water is prepared by mixing 40 parts by weight of active compound with 7 parts by weight of a sulfosuccinic acid monoester, 2 parts by weight of a sodium lignosulfonate and 51 parts by weight of water and grinding in a friction ball mill to a fineness of less than 5 microns.

d) An emulsifiable concentrate can be prepared from 15 parts by weight of active compound, 75 parts by weight of cyclohexanone as solvent and 10 parts by weight of ethoxylated nonylphenol (10 EO) as emulsifier.

e) Granules can be prepared from 2 to 15 parts by weight of active compound and an inert granule carrier material such as attapulgite, pumice granules and/or quartz sand. Expediently a suspension of the wettable powder from Example b) having a solid content of 30 is used and this is sprayed onto the surface of attapulgite granules, dried and mixed intimately. The weight content of the wettable powder here is about 5% and that of the inert carrier material about 95% of the finished granules.

C. Biological examples

Example 1

*Phytophthora infestans*

Tomato plants of the variety "Rheinlands Ruhm" were uniformly wetted in the 3 to 4 leaf stage until dripping wet with aqueous suspensions of the claimed compounds. After drying, the plants were inoculated with a zoosporangia suspension of *Phytophthora infestans* and kept for 2 days under optimum infection conditions in a climatic chamber. Cultivation of the plants was then continued in the greenhouse until expression of symptoms. The assessment of attack was carried out about 1 week after inoculation. The degree of attack on the plants was expressed in leaf area attacked in comparison with the untreated, 100% infected control plants.

With 250 mg of active compound/l of spray liquor the following substances show a complete suppression of attack:

Compounds from Examples 21, 19 and 29

Example 2

*Plasmopara viticola*

Grape seedlings of the varieties "Riesling/Ehrenfelder" were treated until dripping wet with aqueous suspensions of the claimed compounds about 6 weeks after sowing. After drying of the spray coating the plants were inoculated with a zoosporangia suspension of *Plasmopara vitocola* and placed dripping wet for 4 to 5 hours in a climatic chamber at 23° C. and 80 to 90% rel. atmospheric humidity.

After an incubation time of 7 days in the greenhouse, the plants were again placed in the climatic chamber overnight in order to stimulate the sporulation of the fungus. Assessments of attack were then carried out. The degree of attack was expressed in % of attacked leaf area in comparison with the untreated, 100% infected control plants.

With 250 mg of active compound/l of spray liquor the following substances show a complete suppression of attack:

Compounds from Examples 46, 22, 19, 29 and 31

Example 3

*Pyrenophora teres*

Barley plants of the variety "Igri" were treated in the 2-leaf stage until dripping wet with an aqueous suspension of the claimed compounds. After drying of the spray coating the plants were inoculated with an aqueous spore suspension of *Pyrenophora teres* and incubated at 100% rel. atmospheric humidity for 16 hours in a climatic chamber. Cultivation of the infected plants was then continued in a greenhouse at 25° C. and 80% rel. atmospheric humidity.

About 1 week after inoculation the attack was evaluated and the degree of attack assessed in % of attacked leaf area in comparison with untreated, 100% infected controls.

With 250 mg/l of spray liquor the following substance shows complete suppression of attack:

Compound from Example 17

Example 4

*Leptosphaeria nodorum*

Wheat plants of the variety "Jubilar" were treated in the 2-leaf stage until dripping wet with aqueous suspensions of the claimed compounds. After drying of the spray coating the plants were inoculated with an aqueous pyknospore suspension of *Leptosphaeria nodorum* and incubated in a climatic chamber at 100% rel. atmospheric humidity for several hours. Cultivation of the plants was continued in a greenhouse at about 90% rel. atmospheric humidity until expression of symptoms.

About 1 week after inoculation the degree of attack was assessed in % of attacked leaf area in comparison with untreated, 100% infected control plants.

With 250 mg of active compound/l of spray liquor the following substance shows a complete suppression of attack:

Compound from Example 18

Example 5

*Botrytis cinerea*

About 14-day-old field beans of the varieties "Herz Freya" or "Frank's Ackerperle" were treated with aqueous suspensions of the claimed compounds until dripping wet. After drying of the spray coating the plants were inoculated with a spore suspension (1.5 million spores/ml) of *Botrytis cinerea*. Cultivation of the plants was continued in a climatic chamber at 20° to 22° C. and about 99% rel. atmospheric humidity. Infection of the plants manifested itself in the formation of black spots on leaves and stalks. The evaluation of the tests was carried out about 1 week after inoculation. The degree of attack of the plants was assessed in percentage terms to untreated, 100% infected control plants.

With 250 mg of active compound/l of spray liquor the following compounds show a complete suppression of attack:

Compounds from Examples 27, 22, 21, 19, 29, 31, 20 and 30

Example 6

Bean plants (*Phaseolus v.*) heavily attacked by two-spotted spider mites (*Tetranychus urticae*, full population) were sprayed with the aqueous dilution of a wettable powder concentrate which contained 250 ppm of the respective active compound.

The mortality of the mite was checked after 7 days. 100% destruction was achieved using the compounds as in Examples 45, 22, 19, 17 and 19 as the free base.

Example 7

Field beans (*Vicia faba*) heavily infested with black bean aphid (*Aphis fabae*) are sprayed with aqueous dilutions of wettable powder concentrates of 250 ppm active compound content up to the stage of the start of dripping off. The mortality of the aphids is determined after 3 days. A 100% destruction can be obtained using compounds as in Examples 45, 18, 19 and 17.

Example 8

Bean plants heavily infested with greenhouse whiteflies (*Trialeurodes vaporariorum*) were sprayed with aqueous suspensions of wettable powder concentrates (250 ppm active compound content) until dripping off began. After placing the plants in the greenhouse, microscopic checking was carried out after 14 days with the result in each case of 100% mortality with the preparations containing the active compounds of Examples 22, 18, 19, 17 and the free base of 19.

Example 9

L3 larvae of the beetle species *Diabrotica undecimpunctate* were placed on filter paper discs which were saturated with 2 ml each of an aqueous dilution of a wettable powder concentrate which contained 250 ppm of active compound and stored in closed Petri dishes at room temperature (23° C.) for 3 days. The mortality of the larvae was then checked.

100% destruction was achieved with the compound as in Example 18.

We claim:

1. A compound of the formula 1 or its salts

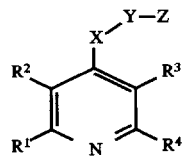

in which (1) $R^1$, $R^2$, $R^3$ and $R^4$ are the same or different radicals selected from the series consisting of:
$(C_1-C_4)$-alkyl,
$(C_2-C_6)$-alkenyl,
$(C_1-C_4)$-alkoxy,
$(C_2-C_6)$-alkenyloxy,
halo-$(C_1-C_4)$-alkyl,
halo-$(C_2-C_4)$-alkenyl,
halo-$(C_1-C_4)$-alkoxy,
halo-$(C_2-C_4)$-alkenyloxy,
R—O—CH$_2$—,
R—O—CO—,
halo-$(C_1-C_6)$-alkoxymethyl,
halo-$(C_2-C_4)$-alkenyloxymethyl,
halo-$(C_1-C_4)$-alkoxycarbonyl,
halo-$(C_2-C_4)$-alkenyloxycarbonyl,
$(C_1-C_4)$-alkylthio,
$(C_2-C_4)$-alkenylthio,
$(C_1-C_4)$-alkylsulfinyl,
$(C_2-C_4)$-alkenylsulfinyl,
$(C_1-C_4)$-alkylsulfonyl,
$(C_2-C_4)$-alkenylsulfonyl,
aryl
substituted amino,
cyano,
halogen and
hydrogen;
R is $(C_1-C_{10})$-alkyl,
$(C_2-C_{10})$-alkenyl,
$(C_2-C_{10})$-alkynyl,
$(C_3-C_8)$-cycloalkyl or aralkyl;
aryl is defined as below under (4);
aralkyl is aryl-$(C_1-C_4)$-alkyl;

(2) X is O, S, NH, NR or NOR, R being defined as above under (1);

(3) Y is a bond or a bivalent hydrocarbon radical having 1 to 6 carbon atoms, in which a methylene group can be replaced by an oxygen atom, and which is optionally substituted by one or more identical or different radicals selected from the series consisting of
$(C_1-C_7)$-alkyl,
$(C_2-C_4)$-alkenyl,
$(C_3-C_4)$-alkynyl,
halo-$(C_1-C_4)$-alkyl and
halogen;

(4) Z is $(C_3-C_8)$-cycloalkyl or $(C_5-C_8)$-cycloalkenyl, it being possible in the carbocycle for one CH$_2$ to be replaced by NR$^5$, and R$^5$ is phenyl or substituted phenyl, which $(C_3-C_8)$-cycloalkyl or $(C_5-C_8)$-cycloalkenyl is substituted by one or more, identical or different radicals wherein at least one of said radicals is in the cis-position with respect to Y, and which radicals are selected from the series consisting of:
$(C_7-C_{18})$-alkyl,
$(C_5-C_{18})$-alkenyl,
$(C_7-C_{12})$-alkoxy,
$(C_5-C_{18})$-alkenyloxy,
$(C_7-C_{12})$-acyl
$(C_5-C_8)$-alkanyloxy,
$(C_5-C_{12})$-alkoxylcarbonyl,
$(C_5-C_{12})$-alkenyloxycarbonyl,
SiR$^6$R$^7$R$^8$,
NR$^9$R$^{10}$,
oxo,
aryl,
$(C_2-C_{18})$-alkanediyl,
$(C_1-C_{18})$-alkanediyldioxy,
$(C_1-C_{13})$-alkyloximino and
$(C_2-C_{18})$-alkylidene, it being possible for alkyl, alkenyl, alkanediyl, alkylidene, alkoxy, alkenyloxy, alkanoyloxy, alkoxylcarbonyl, alkenyloxycarbonyl, alkenediyldioxy or alkyloximino, to be unbranched or branched and one or more methylene groups to be replaced by heteroatoms/groups, selected from the group consisting of O, $NR^{11}$ and $SiR^{12}R^{13}$ and moreover for 3 to 6 carbon atoms to form a cycle, and being optionally substituted by one or more identical or different radicals selected from the series consisting of halogen, halo-$(C_1-C_4)$-alkyl, $(C_3-C_8)$-cycloalkyl, $(C_1-C_8)$-acyl, phenoxy substituted phenoxy, phenyl, substituted phenyl, phenylthio and substituted phenylthio, $R^{11}$ being hydrogen, $(C_1-C_4)$-alkyl or $(C_1-C_4)$-acyl and $R^{12}$ and $R^{13}$ being identical or different and independently of one another being $(C_1-C_4)$-alkyl, phenyl or substituted phenyl, of the said alkyl, alkenyl, alkanediyl, alkylidene and radicals derived therefrom;

$R^6$, $R^7$ and $R^8$ are independently selected from the group consisting of $(C_1-C_4)$-alkyl, phenyl and substituted phenyl and $R^9$, $R^{10}$ are independently selected from the group consisting of $(C_1-C_4)$-alkyl, $(C_3-C_6)$-cycloalkyl, phenyl and substituted phenyl;

aryl is a phenyl group which is optionally substituted by one or more identical or different groups selected from the series consisting of:
halogen,
$(C_3-C_8)$-cycloalkyl,
$(C_3-C_8)$-cycloalkenyl,
phenoxy,
substituted phenoxy,
phenylthio,
substituted phenylthio,
phenyl,
substituted phenyl,
$NO_2$,

acetoxy,
hydroxyl,
cyano,
$SiR^6R^7R^8$,
$O-SiR6^6R^7R^8$,
$NR^{15}R^{16}$,
$S(O)R^{17}$,
$SO_2R^{17}$,
$(C_1-C_{12})$-alkyl,
$(C_1-C_{12})$-alkenyl,
$(C_1-C_7)$-alkoxy and
$(C_1-C_7)$-alkylthio $R^{14}$ is $(C_1-C_7)$-alkyl, halo-$(C_1-C_7)$-alkyl, $(C_3-C_7)$-cycloalkyl, halo-$(C_3-C_7)$-cycloalkyl, $(C_1-C_7)$-alkoxy, phenyl or substituted phenyl;

$R^6$, $R^7$ and $R^8$ have the meaning as above;

$R^{15}$ and $R^{16}$ independently selected from the group consisting of hydrogen, $(C_1-C_4)$-alkyl and $(C_1-C_4)$-acyl;

$R^{17}$ is $(C_1-C_{10})$-alkyl, phenyl or substituted phenyl; in $(C_1-C_{12})$-alkyl and $(C_2-C_{12})$-alkenyl the hydrocarbon chain can be unbranched or branched and one or more $CH_2$ groups can be replaced by heteroatoms/groups selected from the group consisting of O, S, SO, $SO_2$, $NR^{11}$ and $SiR^{12}R^{13}$;

$R^{11}$, $R^{12}$ and $R^{13}$ have the meaning as above;

the $(C_1-C_{12})$-alkyl or $(C_2-C_{12})$-alkenyl radical can additionally be substituted by one or more, identical or different groups selected from the series consisting of halogen, halo-$(C_1-C_4)$-alkoxy, hydroxyl, $(C_3-C_8)$-cycloalkyl, $(C_3-C_5)$-cycloalkenyl, $(C_1-C_4)$-acyl, phenoxy, substituted phenoxy, phenyl, substituted phenyl, phenylthio and substituted phenylthio; $(C_1-C_7)$-alkoxy and $(C_1-C_7)$-alkylthio can be unbranched or branched and one or more $CH_2$ groups therein can be replaced by O, and moreover can be substituted by one or more identical or different groups selected from the series consisting of halogen, phenyl, substituted phenyl, $(C_3-C_8)$-cycloalkyl, $(C_2-C_8)$-cycloalkenyl, phenoxy and substituted phenoxy.

2. A compound of the formula 1 as claimed in claim 1 or its salts in which (1) $R^1$, $R^2$, $R^3$ and $R^4$ are the same or different radicals selected from the series consisting of
$(C_1-C_4)$-alkyl,
$(C_2-C_4)$-alkenyl,
$(C_1-C_4)$-alkoxy,
$(C_2-C_4)$-alkenyloxy,
halo-$(C_1-C_4)$-alkyl,
halo-$(C_2-C_4)$-alkenyl,
halo-$(C_1-C_4)$-alkoxy,
halo-$(C_2-C_4)$-alkenyloxy,
R—O—$CH_2$—,
R—O—CO—,
halo-$(C_1-C_4)$-alkoxymethyl,
halo-$(C_2-C_4)$-alkenyloxymethyl,
halo-$(C_1-C_4)$-alkoxycarbonyl,
halo-$(C_2-C_4)$-alkenyloxycarbonyl,
cyano,
halogen and
hydrogen;

R is defined in claim 1, but only has a maximum of 7 carbon atoms and is not cycloalkyl or aralkyl;

(2) X is O, S or NH;

(3) y is as defined in claim 1;

(4) Z is $(C_3-C_8)$-cycloalkyl or $(C_5-C_8)$-cycloalkenyl, it being possible for one $CH_2$ in the carbocycle to be replaced by $NR^5$, and $R^5$ is phenyl or substituted phenyl, which $(C_3-C_8)$-cycloalkyl or $(C_5-C_8)$-cycloalkenyl is substituted by one or more identical or different radicals selected from the series consisting of
$(C_7-C_{18})$-alkyl,
$(C_5-C_{18})$-alkenyl,
$(C_7-C_{12})$-alkoxy,
$(C_5-C_{18})$-alkenyloxy,
$(C_7-C_{12})$-acyl,
$(C_5-C_{12})$-alkoxycarbonyl,
$(C_5-C_{12})$-alkenyloxycarbonyl,
$SiR^6R^7R^8$,
oxo,
aryl,
$(C_2-C_{18})$-alkanediyl,
$(C_1-C_{18})$-alkanediyldioxy,
$(C_1-C_{13})$-alkyloximino and
$(C_2-C_{18})$-alkylidene, it being possible for alkyl, alkenyl, alkanediyl, alkylidene, alkoxy, alkenyloxy, alkanoyloxy, alkoxylcarbonyl, alkenyloxycarbonyl, alkanediyldioxy or alkyloximino, to be unbranched or branched and one or more methylene groups to be replaced by heteroatoms/groups selected from the group consisting of O, $NR^{11}$ and $SiR^{12}R^{13}$, and moreover for 3 to 6 carbon atoms to form a cycle, and being optionally substituted by one or more identical or different radicals selected from the series consisting of halogen, halo-$(C_1-C_4)$-alkyl, $(C_3-C_8)$-cycloalkyl, $(C_1-C_8)$-acyl, phenoxy, substituted phenoxy, phenyl and substituted phenyl, $R^6$, $R^7$ and $R^8$ are independently selected from the group consisting of $(C_1-C_4)$-alkyl, phenyl and substituted phenyl, and aryl is a phenyl group which is optionally substituted by one or more identical or different groups selected from the series consisting of: halogen,
$(C_3-C_8)$-cycloalkyl,
$(C_3-C_8)$-cycloalkenyl,
phenoxy,
substituted phenoxy,
phenyl,
substituted phenyl,

$SiR^6R^7R^8$,
$O-SiR^6R^7R^8$,
$NR^{15}R^{16}$,
$(C_1-C_{12})$-alkyl,
$(C_1-C_{12})$-alkenyl and
$(C_1-C_7)$-alkoxy, $R^{14}$ is $(C_1-C_7)$-alkyl, halo-$(C_1-C_7)$-alkyl, $(C_5-C_6)$-cycloalkyl, $(C_1-C_7)$-alkoxy, phenyl or substituted phenyl;

$R^6$, $R^7$ and $R^8$ have the meaning as above;

$R^{15}$ and $R^{16}$ are independently selected from the group consisting of hydrogen, $(C_1-C_4)$-alkyl and $(C_1-C_4)$-acyl;

in $(C_1-C_{12})$-alkyl and $(C_2-C_{12})$-alkenyl the hydrocarbon chain can be unbranched or branched and one or more $CH_2$ groups can be replaced by heteroatoms/groups selected from the group consisting of O, $NR^{11}$ and
$SiR^{12}R^{13}$;

$R^{11}$, $R^{12}$ and $R^{13}$ have the meaning as above;

the $(C_1-C_{12})$-alkyl and $(C_2-C_{12})$-alkenyl radical can additionally be substituted by one or more identical or different groups selected from the series consisting of halogen, halo-$(C_1-C_4)$-alkoxy, hydroxyl, $(C_3-C_6)$-cycloalkyl, $(C_1-C_4)$-acyl, phenoxy, substituted phenoxy, phenyl and substituted phenyl;

$(C_1-C_7)$-alkoxy can be unbranched or branched and one or more $CH_2$ groups therein can be replaced by O, and moreover can be substituted by one or more identical or different groups selected from the series consisting of halogen, phenyl, substituted phenyl, $(C_3-C_6)$-cycloalkyl, $(C_3-C_8)$-cycloalkenyl, phenoxy and substituted phenoxy.

3. A compound of the formula 1 as claimed in claim 1 or its salts, in which (1) $R^1$, $R^2$, $R^3$, and $R^4$ are the same or different radicals selected from the series consisting of:
$(C_1-C_3)$-alkyl,
$(C_2-C_3)$-alkenyl,
$(C_1-C_3)$-alkoxy,
$(C_2-C_3)$-alkenyloxy,
halo-$(C_1-C_4)$-alkyl,
halo-$(C_2-C_4)$-alkenyl,
halo-$(C_1-C_4)$-alkoxy,
halo-$(C_2-C_4)$-alkenyloxy,
$R-O-CH_2-$,
$R-O-CO-$,
halo-$(C_1-C_3)$-alkoxymethyl,
halo-$(C_2-C_3)$-alkenloxymethyl,
halo-$(C_1-C_3)$-alkoxycarbonyl,
halo-$(C_2-C_3)$-alkenyloxycarbonyl,
cyano,
halogen and
hydrogen;

R is as defined in claim 1 but only has a maximum of 5 carbon atoms and is not alkynyl, cycloalkyl or aralkyl;

(2) X is O or NH;

(3) Y is a bond or a bivalent hydrocarbon radical having 1 to 6 carbon atoms, in which a methylene group can be replaced by an oxygen atom, and which is optionally substituted by one or more identical or different radicals selected from the series consisting of:
$(C_1-C_3)$-alkyl,
branched $(C_3-C_5)$-alkyl,
halo-$(C_1-C_5)$-alkyl or
halogen;

(4) Z is $(C_3-C_6)$-cycloalkyl, it being possible for one $CH_2$ in the carbocycle to be replaced by $NR^5$ and $R^5$ being phenyl or substituted phenyl, which $(C_3-C_8)$-cycloalkyl is substituted by one or more identical or different radicals selected from the series consisting of:
$(C_7-C_{12})$-alkyl
$(C_5-C_{12})$-alkenyl,
$(C_7-C_{12})$-alkoxy,
$(C_5-C_{12})$-alkenyloxy,
$(C_7-C_{12})$-acyl,
$(C_5-C_{12})$-alkoxycarbonyl,
$(C_5-C_{12})$-alkenyloxycarbonyl,
$SiR^6R^7R^8$,
oxo,
aryl,
$(C_2-C_{18})$-alkanediyl,
$(C_1-C_{18})$-alkanediyldioxy,
$(C_1-C_8)$-alkyloximino and
$(C_2-C_{12})$-alkylidene, it being possible for alkyl, alkenyl, alkanediyl, alkylidene, alkoxy, alkenyloxy, alkanoyloxy, alkoxylcarbonyl, alkenyloxycarbonyl, alkanediyldioxy or alkyloximino to be unbranched or branched and for one or more methylene groups to be replaced by heteroatoms/groups selected from the group consisting of O, $NR^{11}$ and $SiR^{12}R^{13}$ and moreover for 3 to 6 carbon atoms to form a cycle, and being optionally substituted by one or more identical or different radicals selected from the series consisting of halogen, halo-$(C_1-C_4)$-alkyl, $(C_3-C_8)$-cycloalkyl, $(C_1-C_8)$-acyl, phenoxy, substituted phenoxy, phenyl and substituted phenyl, $R^{11}$ being $(C_1-C_4)$-acyl and $R^{12}$ and $R^{13}$ being identical or different and independently of one another being $(C_1-C_4)$-alkyl, phenyl or substituted phenyl, $R^6$, $R^7$ and $R^8$ are independently selected from the group consisting of $(C_1-C_4)$-alkyl, phenyl and substituted phenyl, and aryl is a phenyl group which is optionally substituted by one or more identical or different groups selected from the series consisting of:
halogen,
$(C_5-C_6)$-cycloalkyl,
phenoxy,
substituted phenyoxy,
phenyl,
substituted phenyl,
$SiR^6R^7R^8$,
$O-SiR^6R^7R^8$,
$(C_1-C_{16})$-alkyl and $(C_1-C_7)$-alkoxy, $R^6$, $R^7$ and $R^8$ have the meaning as above;

$R^{15}$ and $R^{16}$ are independently selected from the group consisting of hydrogen, $(C_1-C_4)$-alkyl and $(C_1-C_4)$-acyl;

in $(C_1-C_6)$-alkyl the hydrocarbon chain can be unbranched or branched and one or more $CH_2$ groups can be replaced by heteroatoms/groups selected from the group consisting of O, $NR^{11}$ and $SiR^{12}R^{13}$;

$R^{11}$, $R^{12}$ and $R^{13}$ have the meaning as above; the $(C_1-C_6)$-alkyl radical can additionally be substituted by one or more identical or different groups selected from the series consisting of halogen, $(C_5-C_6)$-cycloalkyl, phenoxy, substituted phenoxy, phenyl and substituted phenyl; $(C_1-C_7)$-alkoxy can be unbranched or branched and one or more $CH_2$ therein can be replaced by O and moreover can be substituted by one or more identical or different groups selected from the series consisting of halogen, phenyl, substituted phenyl, $(C_5-C_6)$-cycloalkyl, phenoxy and substituted phenoxy.

4. A compound of the formula 1 as claimed in claim 1 or its salts, in which the substituent(s) of cycloalkyl or cycloalkenyl defined under (4) is/are in the cis-position with respect to Y.

5. A compound of the formula 1 as claimed in claim 4 or its salts, in which Z is cyclohexyl substituted once in the 4-position.

6. A fungicidal composition containing a fungicidally active amount of at least one compound as claimed in claim 1 together with the additives or auxiliaries customary for this application.

7. An insecticidal, acaricidal or nematicidal composition, containing an active amount of at least one compound as claimed in claim 1 together with the additives or auxiliaries customary for these applications.

8. A plant protection agent, containing a fungicidally, insecticidally, acaricidally or nematicidally active amount of at least one compound as claimed in claim 1 and at least one further active compound from the fungicides, insecticides, baits, sterilants, acaricides, nematicides and herbicides series together with the auxiliaries and additives customary for this application.

9. A composition for use in wood preservation or is a preservative in sealing compositions, in painting colors, in cooling lubricants for metal processing or in drilling and cutting oils, containing an active amount of at least one compound as claimed in claim 1 together with the auxiliaries and additives customary for these applications.

10. A veterinary pharmaceutical for the control of endo- or ectoparasites containing an effective amount for this application of a compound as claimed in claim 1 and a physiologically acceptable carrier.

11. A seed, treated or coated with an effective amount of at least one compound or of a composition containing an effective amount of the at least one compound, wherein the at least one compound is as claimed in claim 1.

* * * * *